United States Patent
Seidel et al.

(10) Patent No.: US 11,759,460 B2
(45) Date of Patent: Sep. 19, 2023

(54) METHOD OF LOCAL ANTIBIOTIC TREATMENT OF INFECTIVE ENDOCARDITIS

(71) Applicant: DEVIE MEDICAL GMBH, Jena (DE)

(72) Inventors: Raphael A. Seidel, Jena (DE); Hans R. Figulla, Jena (DE); Kristina M. Tramm, Jena (DE)

(73) Assignee: DEVIE MEDICAL GMBH, Jena (DE)

( * ) Notice: Subject to any disclaimer, the term of this patent is extended or adjusted under 35 U.S.C. 154(b) by 330 days.

(21) Appl. No.: 16/994,314

(22) Filed: Aug. 14, 2020

(65) Prior Publication Data

US 2022/0047584 A1    Feb. 17, 2022

(51) Int. Cl.
 A61K 31/496    (2006.01)
 A61K 9/00    (2006.01)
 A61K 38/14    (2006.01)

(52) U.S. Cl.
 CPC .......... *A61K 31/496* (2013.01); *A61K 9/0024* (2013.01); *A61K 38/14* (2013.01)

(58) Field of Classification Search
 CPC ..... A61K 31/496; A61K 9/0024; A61K 38/14
 See application file for complete search history.

(56) References Cited

U.S. PATENT DOCUMENTS

| 5,861,157 A | 1/1999 | Burnie et al. |
| 2005/0228496 A1 | 10/2005 | Mensah et al. |
| 2006/0276813 A1 | 12/2006 | Greenberg |
| 2007/0156233 A1 | 7/2007 | Kapadia et al. |
| 2009/0264991 A1 | 10/2009 | Paul, Jr. et al. |
| 2011/0275912 A1 | 11/2011 | Lauten et al. |
| 2012/0136430 A1 | 5/2012 | Sochman et al. |
| 2013/0150957 A1 | 6/2013 | Weber |
| 2013/0197622 A1 | 8/2013 | Mitra |

(Continued)

FOREIGN PATENT DOCUMENTS

| CA | 2961837 A1 | 3/2016 |
| DE | 502014003291.7 | 4/2017 |

(Continued)

OTHER PUBLICATIONS

Falcone et al, Optimizing antibiotic treatment of bacteremia and endocarditis due to staphylococci and enterococci: Ne Insights and Evidence from Literature, Journal of Infection and Chemotherapy, vol. 21, No. 5, pp. 330-339. (Year: 2018).*

(Continued)

*Primary Examiner* — Carlos A Azpuru
(74) *Attorney, Agent, or Firm* — Squire Patton Boggs (US) LLP

(57) ABSTRACT

A method of treating or preventing endocarditis in a human patient in need of therapy is disclosed. The method comprises identifying a patient inflicted with or being at risk of contracting *Staphylococcus aureus, Enterococcus faecalis,* or *Enterococcus faecium;* and locally delivering to or in the vicinity of a heart valve a therapeutically or prophylactically effective amount of rifampicin, daptomycin, dalbavancin, vancomycin, or gentamycin, or a combination of rifampicin, daptomycin, dalbavancin, vancomycin, and gentamycin. The method comprises treatment or prevention of a bacterial biofilms on the endocardium caused by *Staphylococcus aureus, Enterococcus faecalis,* or *Enterococcus faecium.*

14 Claims, 21 Drawing Sheets

(56) References Cited

U.S. PATENT DOCUMENTS

| | | |
|---|---|---|
| 2013/0261739 A1 | 10/2013 | Kuehn |
| 2013/0331929 A1 | 12/2013 | Mitra et al. |
| 2014/0114402 A1 | 4/2014 | Ahlberg et al. |
| 2014/0114407 A1 | 4/2014 | Rajamannan |
| 2015/0282958 A1 | 10/2015 | Centola et al. |
| 2015/0305860 A1 | 10/2015 | Wang et al. |
| 2018/0000579 A1 | 1/2018 | Lauten et al. |
| 2018/0098843 A9 | 4/2018 | Lauten et al. |
| 2018/0147056 A1 | 5/2018 | Lauten et al. |
| 2019/0394643 A1 | 12/2019 | Townend |
| 2020/0222182 A1* | 7/2020 | Lauten .................. A61F 2/2427 |
| 2020/0230081 A1 | 7/2020 | Pathak |

FOREIGN PATENT DOCUMENTS

| | | |
|---|---|---|
| EP | 3000436 B1 | 4/2017 |
| EP | 2929860 B1 | 6/2017 |
| WO | 200/076890 A1 * | 7/2006 |
| WO | WO 2006/076890 A1 | 7/2006 |
| WO | WO 2008/070797 A1 | 6/2008 |
| WO | WO 2016/045808 A1 | 3/2016 |
| WO | WO 2020/074130 A1 | 4/2020 |

OTHER PUBLICATIONS

International Search Report and Written Opinion for International PCT application No. PCT/EP2021/053010, dated Apr. 20, 2021, 17 pages.

Ahola et al., "Processing and Sustained in Vitro Release of Rifampicin Containing Composites to Enhance the Treatment of Osteomyelitis", Biomatter, vol. 2, No. 4, Oct. 1, 2012, pp. 213-225.

Falcone et al., "Optimizing Antibiotic Therapy of Bacteremia and Endocarditis Due to Staphylococci and Enterococci: New Insights and Evidence From Literature", Journal of Infection and Chemotherapy, vol. 21, No. 5, May 1, 2015, pp. 330-339.

Kuehn et al., "Prevention of Early Vascular Graft Infection Using Regional Antibiotic Release", Journal of Surgical Research, vol. 164, No. 1, Nov. 1, 2010, pp. e185-e191.

Mashaqi et al., "Antibiotic Pretreatment of Heart Valve Prostheses to Prevent Early Prosthetic Valve Endocarditis", Journal of Heart Valve Disease, 2011, vol. 20:582-586.

U.S. Appl. No. 62/743,828, filed Oct. 10, 2018, Figulla et al.

R.Seidel: Devie Medical GmbH, Presentation: Katheterbasierte Therapie entzundlicher Herzklappenerkrankungen, Vielen Dank Fur Ihre Aufmerksamkeit, Devie Medical GMBH; 25 pages, with translation, Apr. 5, 2017 (See European Patent EP 3000436, issued Apr. 5, 2017).

Hans R. Figulla, MD, Proffessor of Medicine (Emeritus) Friedrich Schiller University, Jena Germany, Endocarditis: An Ongoing Health Burden, 50 pages, Presentation given at the CRTmeeting Washington D.C. Feb. 25, 2020.

Hans R. Figulla, MD, Proffessor of Medicine (Emeritus) Friedrich Schiller University, Jena Germany, Vortrag_Endokarditis Washington 2019 Powerpoint presentation, CRT19, CRTOnline.org., Infectious Endocarditis: A Field for Interventional Therapy, 23 pages, 2019.

PCT International Search Report and Written Opinion for International Application No. PCT/EP2014/065294 dated Mar. 6, 2015, with translation, 20 pages.

PCT International Search Report and Written Opinion for International Application No. PCT/EP2015/064745 dated Jul. 17, 2015, with translation, 22 pages.

\* cited by examiner

METHOD OF LOCAL ANTIBIOTIC TREATMENT OF INFECTIVE ENDOCARDITIS

FIELD

The embodiments of the invention relate to methods of treating or preventing infective endocarditis.

BACKGROUND

Infective endocarditis (IE) is a serious disease with approximately 20% mortality rate within 30 days. The condition is caused by a bacterial infection on heart valve leaflets and/or surrounding tissue. The disease can occur or appear spontaneously or in persons at risk, such as those with valvular heart disease or those receiving any replacement of an artificial heart valve. The underlying bacterial infection can, in turn, induce cardiac valve dysfunction, bacterial embolic stroke, or embolic impacts in other organs. In severe cases, IE can cause septic multi-organ dysfunction and failure. The disease prognosis is unchanged since several decades. The present treatment methods involve resecting the diseased heart valves and replace those with new prosthetic or homograft valves, with supporting oral or intravenous antibiotic treatment. Systemic administration is typically at a high dose and for a period of weeks. About 25% of patients are treated exclusively by long-term antibiotic treatment either because patients are too sick for a surgical open chest heart valve replacement therapy or because the disease is detected at an early stage with minor aggressive bacteria such as Streptococcus viridans.

Transcatheter valve replacement therapy, including transcatheter aortic valve replacement (TAVR) and transcatheter mitral valve replacement (TMVR) is contraindicated in IE, because this therapy does not resect the bacterial infectious focus, or reduce or eliminate the bacteria, and instead partly encapsulates the infective tissue. This encapsulation makes it even more difficult for antibiotic diffusion from the circulation into the bacterially infected tissues. Thus, there is a need in the art for improved methods, compositions, formulations, and devices for treating patients having IE.

SUMMARY

The present invention meets these and other needs in the art. The inventors have found that local application of certain antibiotics and their combinations provide effects or additive effects for the treatment and/or prevention of infective endocarditis (IE). In some embodiments, the methods, compositions, formulations, or devices described herein find particular use in controlling, reducing, or preventing bacterial biofilms that are involved in, associated with, or cause IE. In some cases, the local delivery can be performed by implanting an antibiotic-eluting device at or near a site of IE. In some cases, antibiotic-eluting device is configured to deliver a high dose of one or more antibiotics for an extended period of time. In one aspect the invention is drawn to a method of treating or preventing endocarditis in a human patient in need of therapy, comprising identifying a patient inflicted with or being at risk of contracting *Staphylococcus aureus, Enterococcus faecalis,* or *Enterococcus faecium* at or about (i.e., in vicinity of) a heart valve, and locally delivering to or in the vicinity of the heart valve a therapeutically or prophylactically effective amount of rifampicin, daptomycin, dalbavancin, vancomycin, gentamicin or any combination of 2 or more of these antibiotics. In some embodiments, the antibiotics can be quinolone antibiotics (e.g., fluoroquinolones) and/or penicillinase-resistant beta-lactam antibiotics (e.g., oxacilline), used alone or with any one or combination of rifampicin, daptomycin, dalbavancin, vancomycin, or gentamicin. Any of the aforementioned agents or antibiotics can also include a pharmaceutically acceptable salt or ester thereof. Derivatives or analogs of these antibodies can also be used and falls within the scope of the invention. Any of the aforementioned agents or antibiotics, or pharmaceutically acceptable salt or ester thereof, including derivatives and analogs, can be mixed, added, dispersed, or combined together with one or more pharmaceutically acceptable excipients or carriers.

In one aspect the invention is drawn to a method of treating or preventing endocarditis with a device, which provides a directed release of antibiotics to the site of infection by separating a drug-releasing part of the device as well as the infected tissue (e.g. biofilms and vegetations) from the bloodstream.

In one aspect, the present invention is drawn to a method of treating a subject having IE or at risk of IE with a transcutaneously implantable cardiac valve by performing a transcatheter valve replacement/insertion and simultaneously or sequentially administering a local dose (e.g., high dose) of one or more antibiotics.

BRIEF DESCRIPTION OF THE DRAWINGS

For proper understanding of example embodiments, reference should be made to the accompanying drawings, wherein.

DETAILED DESCRIPTION

Figure 1A:
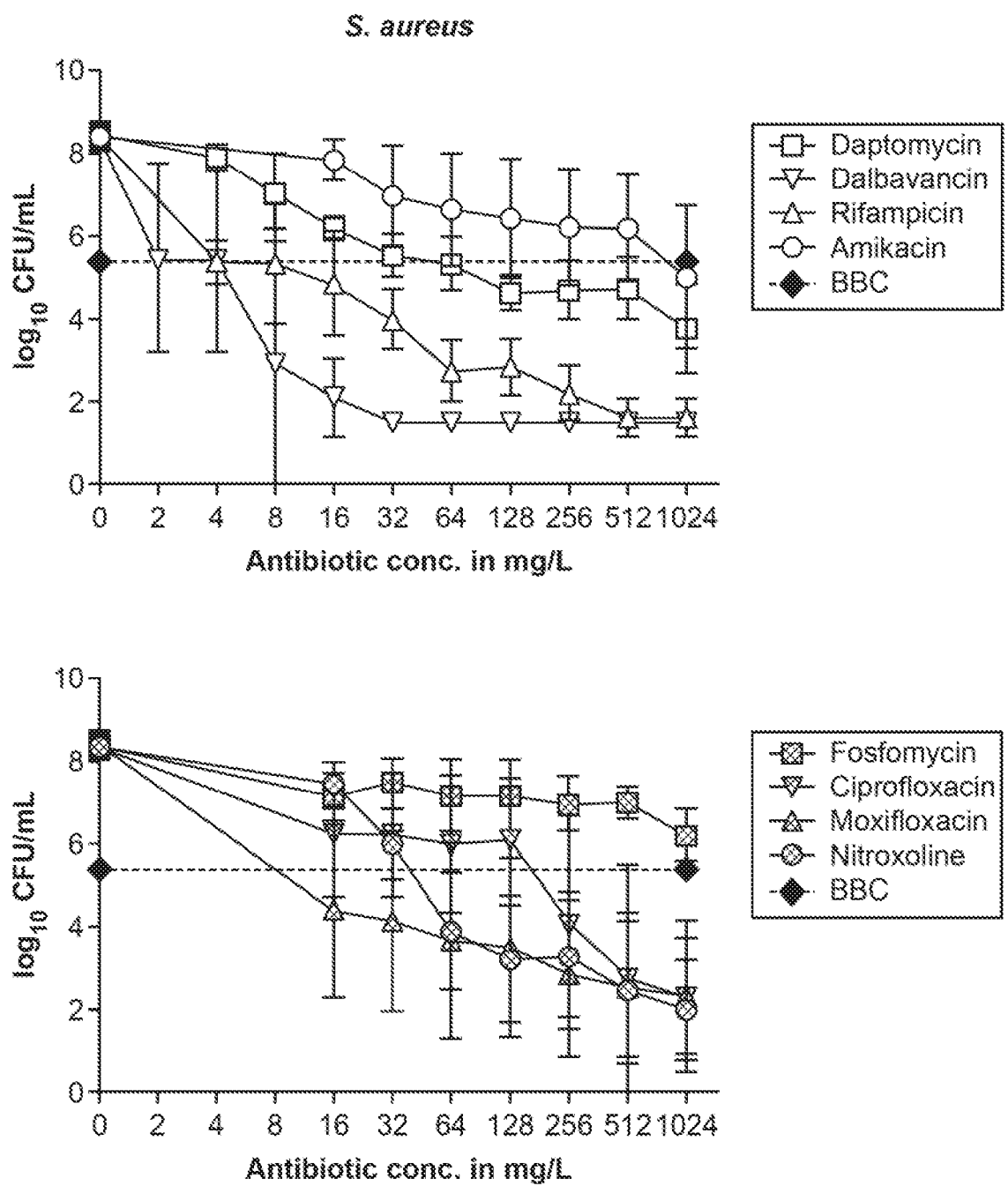
FIGS. 1A and 1B illustrates effects of different antibiotics tested in a dose-dependent manner against bacterial biofilms of different isolates of *S. aureus* and *E. faecalis* using only one antibiotic per treatment to screen the effect of the single antibiotics against bacterial biofilms. The graphs show the decadic logarithm of the colony forming units ($\log_{10}$ CFU) of either *S. aureus* or *E. faecalis* on the ordinate in relation to the concentration of various antibiotics on the abscissa. Data points belonging to one antibiotic were connected by lines for clarity. In each graph, the dashed line reflects the biofilm bactericidal concentration (BBC), defined as the target of 3 $\log_{10}$ CFU below the control, i.e. the $\log_{10}$ CFU of untreated biofilms (shown at the antibiotic concentration of 0 mg/L), which needs to be undercut to achieve a meaningful suppression of the bacteria in a biofilm of ≥99.9%. The line graphs intersecting this line indicate the antibiotics' concentrations that need to be applied for effective treatment in *S. aureus* and *E. faecalis* biofilms. For the treatment of both, *S. aureus* and *E. faecalis*, daptomycin, rifampicin and dalbavancin can suppress the bacteria sufficiently, while the other tested antibiotics candidates do not sufficiently eradicate bacteria in biofilms. For instance, the BBC of rifampicin against *S. aureus* is ~4 mg/L; the BBC of dalbavancin is ~32 mg/L against *E. faecalis* in biofilms.

Described herein are methods, devices, formulations, and compositions for locally preventing or treating infective endocarditis (IE). IE is an infection at the heart valves or endocardium. IE is caused by bacterial infection of cardiac tissue, such as cardiac valve tissue or tissue near or surrounding a cardiac valve, where the bacteria usually appear in bacterial biofilms, and also in the form of so-called vegetations, i.e. macroscopic structures that may consist of various matrix components from blood, tissue, cells, and bacteria and that contain viable bacteria. Described herein is a method of treating or preventing infectious endocarditis (IE). The method comprises identifying a patient inflicted with or being at risk of contracting *Staphylococcus aureus*, *Enterococcus faecalis*, or *Enterococcus faecium*; and local delivery to or in the vicinity of a heart valve a therapeutically or prophylactically effective amount of rifampicin, daptomycin, dalbavancin, vancomycin, or gentamycin, or a combination (i.e., at least 2) of rifampicin, daptomycin, dalbavancin, vancomycin, and gentamycin to treat or prevent endocarditis. In some embodiments, the antibiotics can be quinolone antibiotics (e.g., fluorochinolone) and/or penicillinase-resistant beta-lactam antibiotics (e.g., oxacilline), used alone or with any one or combination of rifampicin, daptomycin, dalbavancin, vancomycin, or gentamicin. Derivatives or analogs of these drugs can also be used and within the scope of the invention. Any of the aforementioned agents or antibiotics can also include a pharmaceutically acceptable salt or ester thereof. Any of the aforementioned agents or antibiotics, or pharmaceutically acceptable salt or ester thereof, including the derivatives or analogs, can be mixed, added, dispersed, or combined together with one or more pharmaceutically acceptable excipients or carriers.

Stated differently, described herein is a method for the prophylaxis and/or treatment of endocarditis in a mammal (e.g., human) suffering from or susceptible to suffering from *Staphylococcus aureus*, *Enterococcus faecalis*, or *Enterococcus faecium* infection, wherein the method comprises locally administering to a heart tissue of the mammal an effective amount of one or a combination of agent selected from the group consisting of rifampicin, daptomycin, dalbavancin, vancomycin, gentamycin, quinolone antibiotics (e.g., fluoroquinolones), penicillinase-resistant beta-lactam antibiotics (e.g., oxacilline), or a pharmaceutically acceptable salt or ester thereof, and optionally together with one or more pharmaceutically acceptable excipients or carriers. Stated differently, described herein is a therapeutically or prophylactically effective amount of one or a combination of an antibiotic selected from the group consisting of rifampicin, daptomycin, dalbavancin, vancomycin, gentamycin, quinolone antibiotics (e.g., fluoroquinolones), penicillinase-resistant beta-lactam antibiotics (e.g., oxacilline), or a pharmaceutically acceptable salt or ester thereof, and optionally together with one or more pharmaceutically acceptable excipients or carriers, for use in the treatment or the prevention of endocarditis in a mammal (e.g., human), wherein the mammal is identified to be inflicted with or being at risk of contracting *Staphylococcus aureus, Enterococcus faecalis*, or *Enterococcus faecium* at or about (e.g., close vicinity) a heart valve, and wherein the antibiotic is for local delivery to or in the close vicinity of the heart valve. The local administration or delivery according to all embodiments disclosed herewith can by an implantable medical device (e.g., implantable valves disclosed herewith), for example with a drug delivery or eluting polymer matrix or coating on the device.

As used herein, antibiotic agent refers to any substance that, when administered in a therapeutically effective amount to a human patient suffering from IE, has a therapeutic beneficial effect on the health and well-being of the patient. A therapeutic beneficial effect on the health and well-being of a patient includes, but is not limited to: (1) curing IE; (2) slowing the progress of IE; (3) causing IE to retrogress; or (4) alleviating one or more symptoms of IE.

As used herein, the antibiotic agent refers to any substance that when administered to a patient, known or suspected of being particularly susceptible to IE (e.g., high risk patient), in a prophylactically effective amount, has a prophylactic or preventative beneficial effect on the health and well-being of the patient. At risk persons can include persons that are subject to receiving an artificial heart valve prosthesis, people that have valvular stenosis, or peoples with general heart valve destruction or degeneration.

A prophylactic or preventative beneficial effect on the health and well-being of a patient includes, but is not limited to: (1) preventing or delaying on-set of the disease or condition in the first place; (2) maintaining the disease or condition at a retrogressed level once such level has been achieved by a therapeutically effective amount of a substance, which may be the same as or different from the substance or substance combination used in a prophylactically effective amount; or, (3) preventing or delaying recurrence of the disease or condition after a course of treatment with a therapeutically effective amount of a substance, which may be the same as or different from the substance or substance combination used in a prophylactically effective amount, has concluded.

Figure 6A:
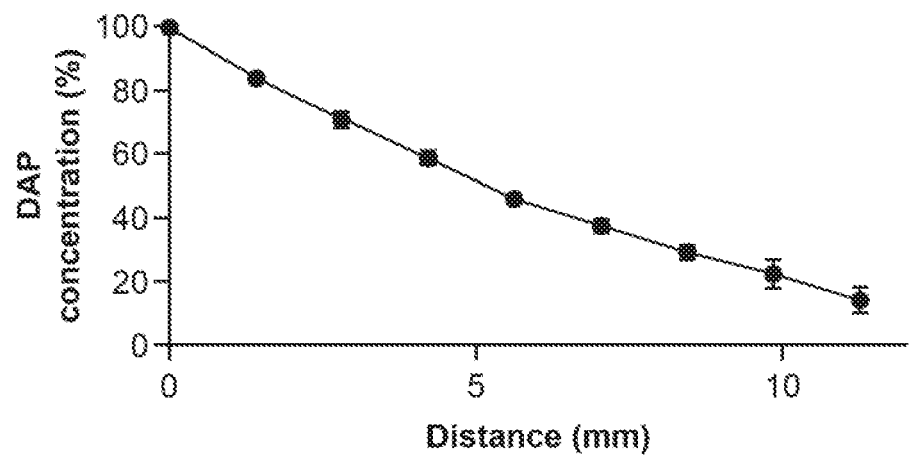
FIGS. 6A and 6B illustrate the diffusion characteristics of the antibiotics daptomycin (A) and rifampicin (B) in a phosphate-buffered collagen matrix at physiological pH. Daptomycin (A) and rifampicin (B) started diffusion with a concentration of 1000 mg/L from the distance d=0 mm into the matrix at the time t=0 h. The graphs illustrate the relative concentration distribution of the antibiotics at t=24 h dependent on the distance to the starting line. Data points reflect the mean of 4 individual experiments where error bars show the standard deviation. Diffusion of both antibiotics into the collagen matrix is roughly similar, albeit the relative rifampicin concentrations are slightly higher.
Figure 6B:
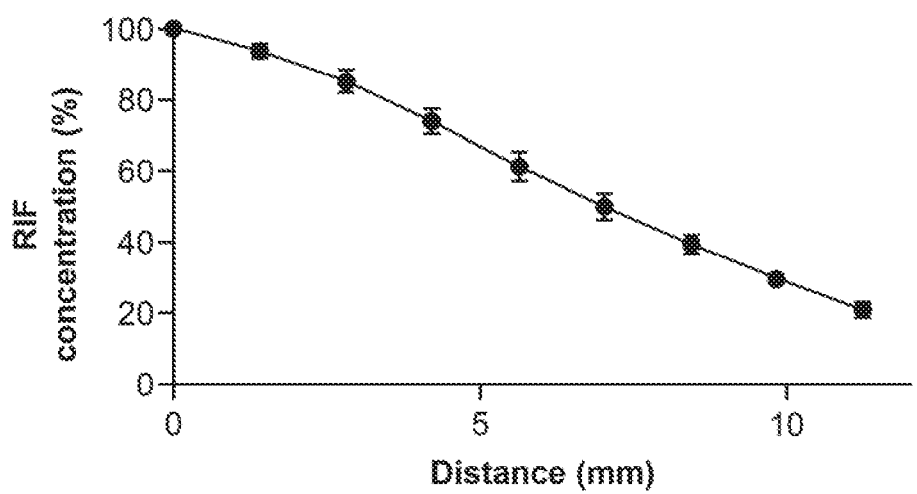
Figure 7:
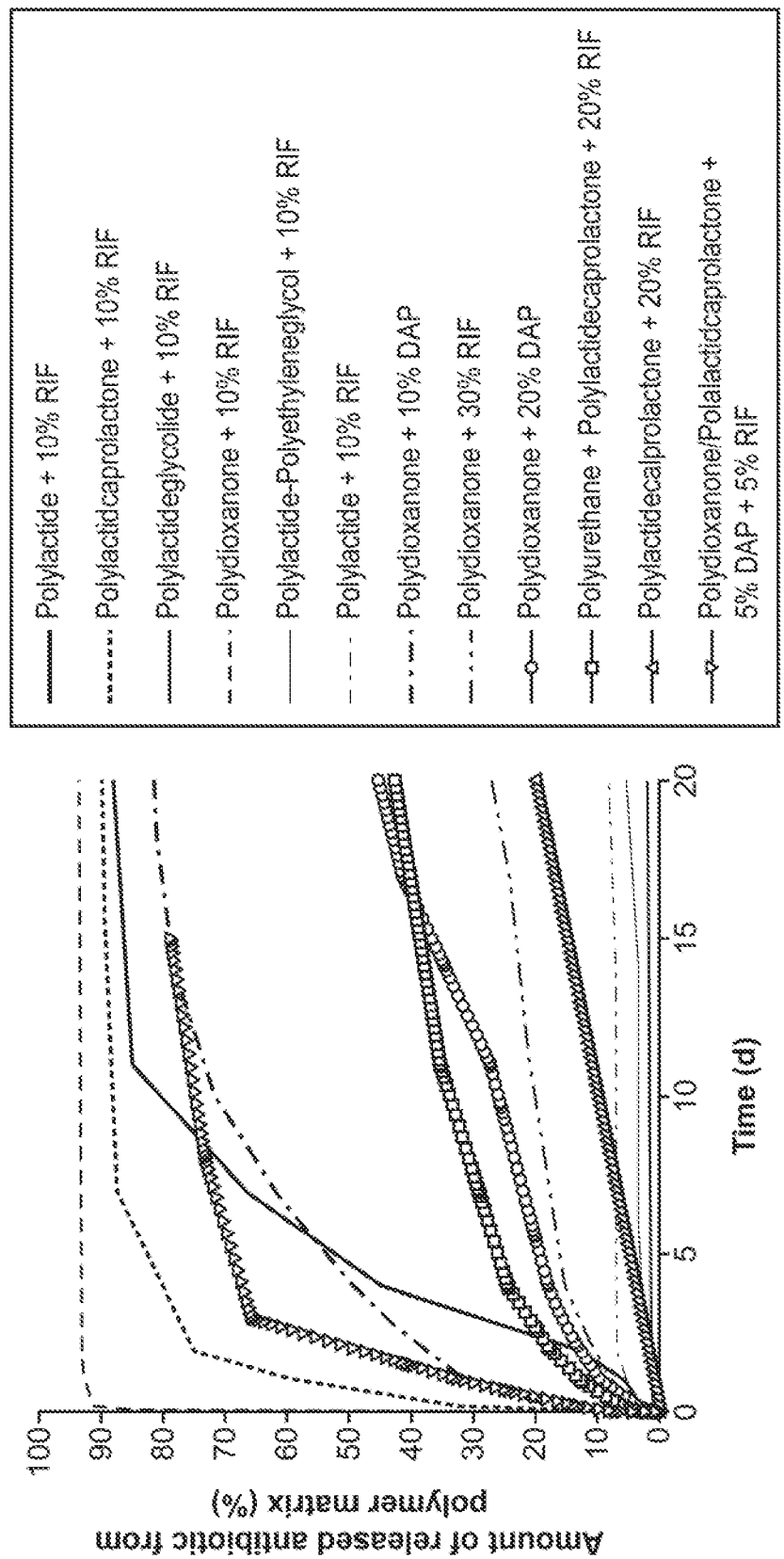
FIG. 7 illustrates various release kinetics of antibiotics daptomycin and rifampicin (DAP and RIF) from different polymeric matrices and in different processing forms, e.g. electrospun non-wovens, thin films, etc., into physiological buffered saline solution at pH 7.4 over time. The kinetics show the cumulative release from polymer-drug-combinations and are given to represent that the release of antibiotics depends on many factors (e.g. polymer type and composition, antibiotic, relative amount of antibiotics, processing techniques, etc.) and needs to be adjusted according to the specific requirements. In one exemplary embodiment, for therapeutic purposes a release of the bulk part of the antibiotic(s) can be approximately within 20 days, whereas for prophylactic purposes within 20 days only up to 50% of the antibiotic(s) should be released.

As used herein, a "therapeutically effective amount" refers to that amount of an antibiotic agent that will have a beneficial effect, which may be curative or palliative, on the health and well-being of the patient so afflicted. A therapeutically effective or prophylactically effective amount may be administered as a single local bolus, but preferably as short-term or long-term local sustained release formulations. The concentration of an antibiotic or a combination of antibiotics in a given ratio to achieve such reduction of the bacterial number, given experimentally as the colony-forming units (CFU) is called the biofilm bactericidal concentration (BBC) in case the bacteria to be eradicated are in biofilms, or the minimal inhibitory concentration (MIC) in the case of planktonic bacteria that are not in a biofilm. As used herein, short-term sustained release refers to the local administration or delivery of an effective amount of an antibiotic agent (or combination of agents) so that at least about 50% or preferably at least about 80% (i.e., 50% to 100% or 80% to 100%) of the total amount of antibiotics to be administered is released within 3 to 21 day, preferably 3 to 14 days. The total amount of antibiotic can be, for example, 10-80 milligrams or more narrowly 20-50 milligrams. The concentration can be adjusted to eradicate >99% (e.g., 99.9%) of Staphylococcus and/or Enterococcus species in biofilms or for prophylactic purposes. As used herein, long-term sustained release refers to the local administration or delivery of an effective amount of an antibiotic agent (or combination of agents) so that at least about 50% or preferably at least about 80% (i.e., 50% to 100% or 80% to 100%) of the total amount of antibiotics to be administered is released within 14 or 21 days to 4 months. The total amount of antibiotic can be, for example, 10-80 milligrams or more narrowly 20-50 milligrams. The concentration can be adjusted to eradicate >99% (e.g., 99.9%) of Staphylococcus and/or Enterococcus species in biofilms or for prophylactic purposes. The unilateral diffusion distance of daptomycin and rifampicin within 24 hours in a collagen matrix is show in FIGS. 6A and 6B. In the prophylactical long-term application the concentration is adjusted to such an inhibitory/bactericidal concentration that planktonic Staphylococcus and/or Enterococcus species are inhibited to form biofilms. In one embodiment, examples for therapeutical short-term release kinetics and for prophylactic long-term release kinetics of rifampicin and daptomycin are shown in FIG. 7 with different polymer carriers.

In some preferred embodiments, the local administration of the antibiotic substance can range from 3 days to 4 months, or any time between.

Figure 8:
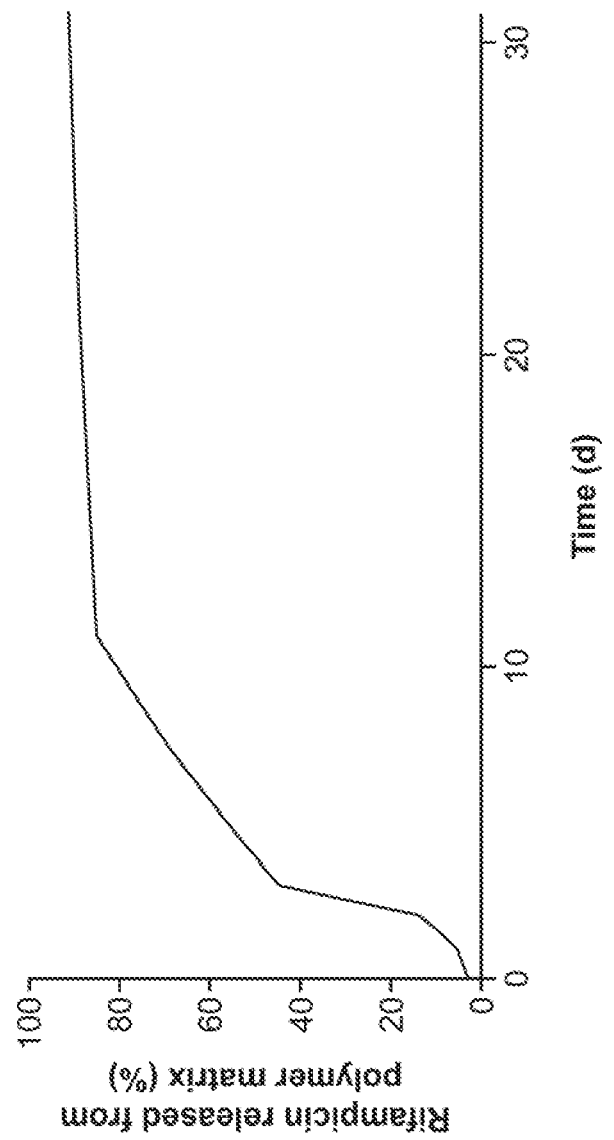
FIG. 8 gives an example of a therapeutic short-term release kinetics of rifampicin embedded in a polyester (PLC7015, poly(lactid-caprolactone)).
Figure 9A:
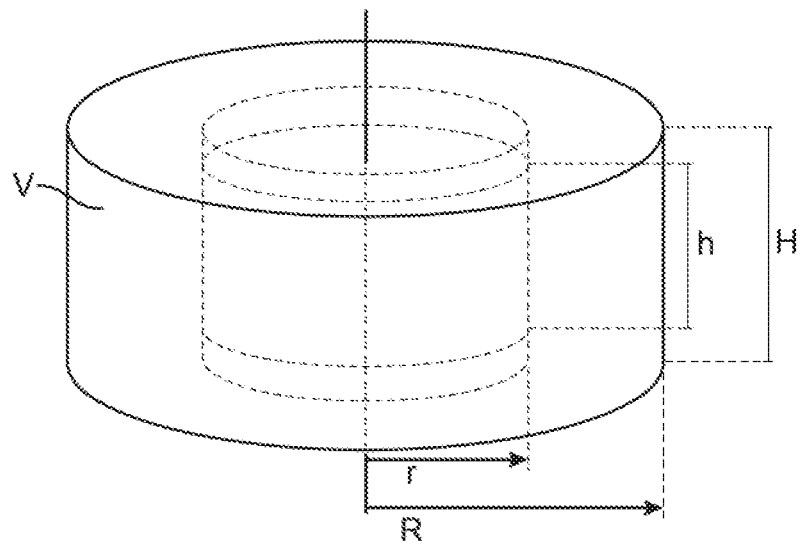
FIGS. 9A and 9B describes a theoretical model for the calculation of the target volumes that will be addressed for local therapy or prophylaxis. It is done under the assumption that the diffusion is unidirectional due to an impermeable layer on the vessel side (luminal side), which is impermeable for the antibiotics. The drug-releasing layer, including the impermeable is exemplarily given as d=0.1 mm (e.g., 0.01 mm to 1.0 mm). 9B illustrates a cross section under the assumption that the bacterial infection is spread around the heart valve or vessel in a cylindrical ring-shaped volume with a radius exceeding 10 mm the radius of the heart valve (r=12.5 mm) and with a height (H) of 20 mm and that the local therapeutic device has a height h=12 mm, the tissue volume to be treated is 22 mL.
Figure 9B:
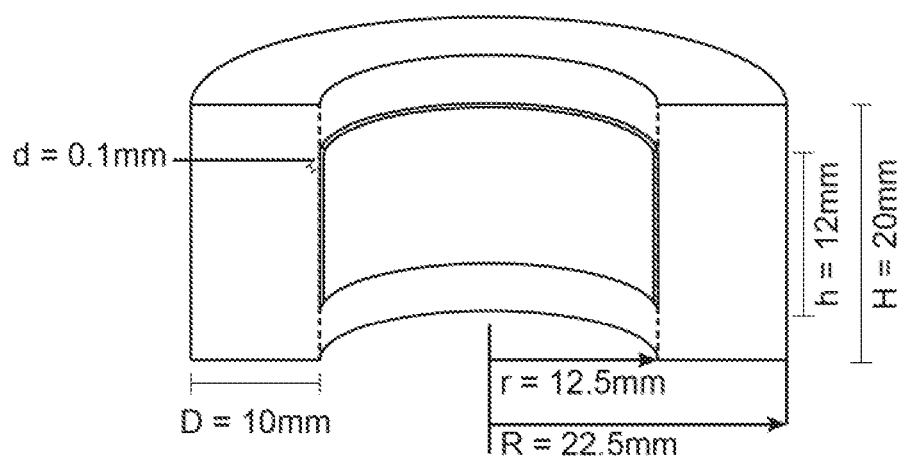
Figure 11:
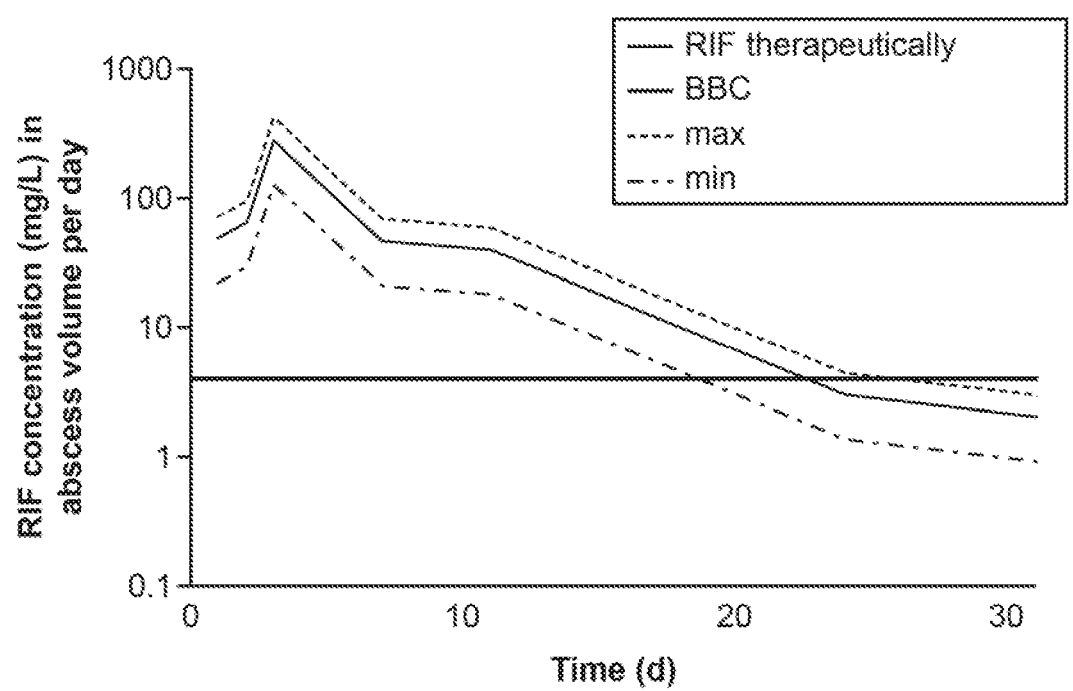
FIG. 11 represents a concentration profile of rifampicin (RIF) for therapeutic short-term release in an assumed cylindrical ring-shaped volume (abscess) of 22 mL (as calculated, see FIG. 9B) around a vessel or heart valve over time. On the basis of the release kinetics shown in FIG. 8 into the tissue volume, RIF concentrations were calculated under the assumption that the amount of daily RIF release from the device into this volume to be treated is equivalent to daily RIF clearance from this volume. For effective treatment of S. aureus biofilms the calculated concentrations must be above the biofilm bactericidal concentration (BBC) of ~4 mg/L shown in the solid horizontal line. The calculation shows that the rifampicin concentration generated from the local release into this volume is above the BBC for more than 20 days. If in contrast to a homogeneous distribution of the antibiotics the diffusion from the antibiotic-releasing matrix into the cylindrical volume is taken into account, there will be a concentration gradient from the inner (central) to the outer (peripheral) layers of the cylinder. The maximal (max) and minimal (min) concentrations are calculated according to the daily diffusion distance of rifampicin in a phosphate-buffered collagen matrix according to FIG. 6B and reflect the concentric spatial distribution of the antibiotics' concentrations within the defined cylindrical volume. The BBC line reflects the biofilm bactericidal concentration of rifampicin from FIGS. 1 and 2.

In one exemplary embodiment, the drug-releasing device can contain approximately 18.8 mg rifampicin (e.g., 20% by weight of rifampicin in 100 µm polymer layer, diameter of device (stent) frame=25 mm and height=12 mm) with the release kinetics for the therapeutic approach (FIG. 8) demonstrates that 80% can be released within 14 days. Referring to FIGS. 9A and 9B, assuming that infective endocarditis has an extension of 10 mm in a cylindrical ring-shaped volume around the vessel or heart valve (with a diameter of 25 mm and the antibiotic is accumulating only in this volume (e.g., 22.0 mL) within one day, the maximal concentration would be 18.8 mg in 22.0 mL equal to 855 mg/L. However, when the release kinetics for a short-term treatment is taken into account (FIG. 8) the concentration profile per day is shown in FIG. 11. According to FIG. 1, it is demonstrated that this calculated concentration is far higher than the concentration necessary to eradicate 99.9% of Staphylococcus aureus in biofilms (BBC~4 mg/L for rifampicin against S. aureus).

Figure 12A:
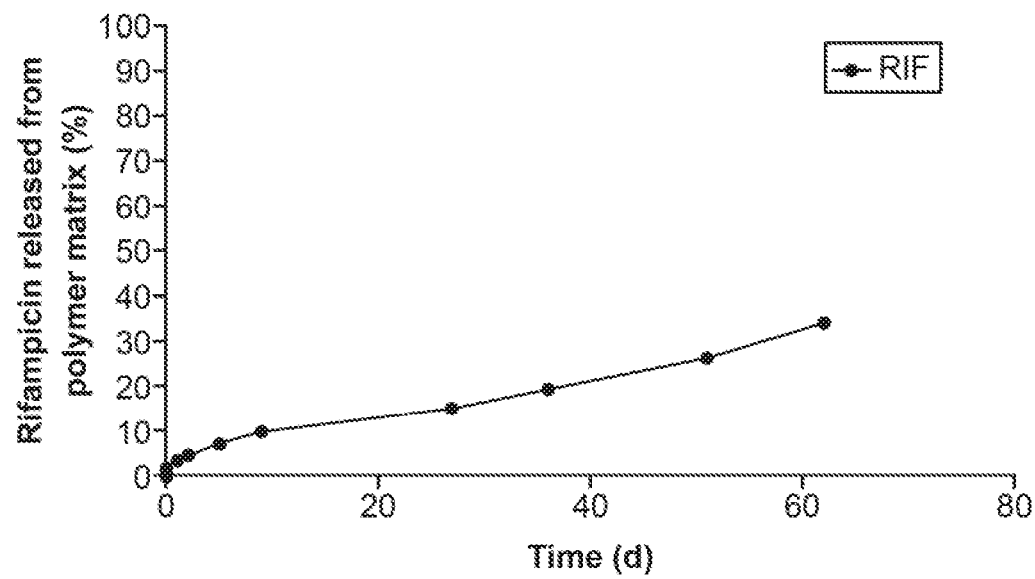
FIG. 12A gives an example of a prophylactic long-term release kinetics of rifampicin embedded in a polydioxanone (poly-p-dioxanone, X206S) matrix, shown as cumulative rifampicin release over time.
Figure 12B:
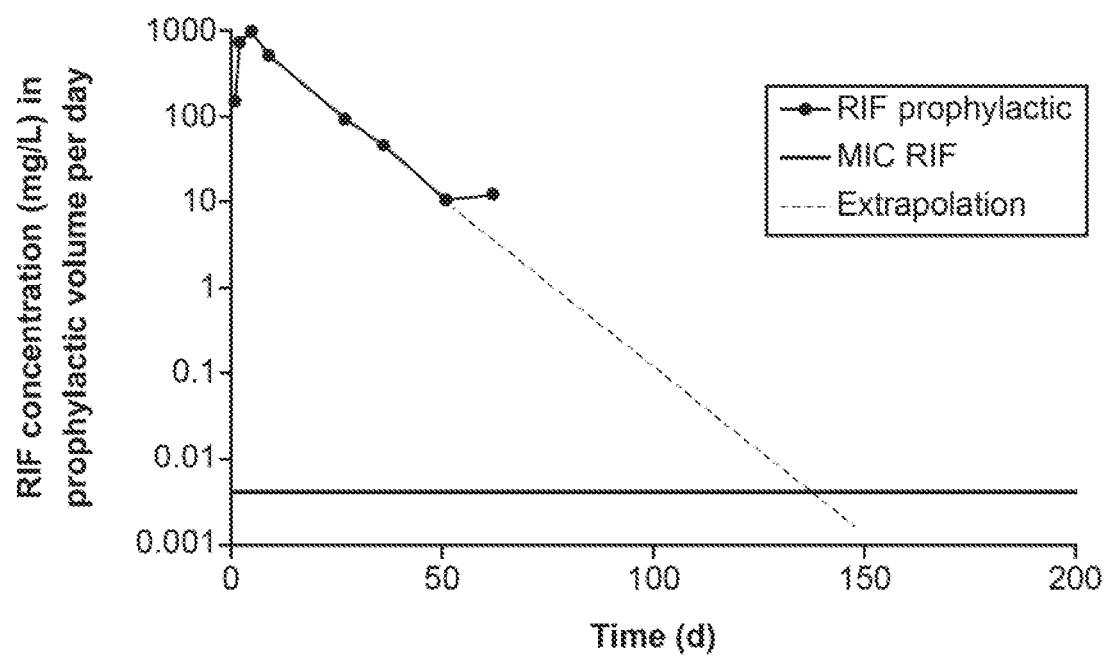
FIG. 12B illustrates a prophylactic long-term concentration profile of rifampicin (RIF) in an assumed cylindrical ring-shaped volume of 1.63 mL (as calculated, see FIG. 10) around a vessel or heart valve over time. On the basis of the release kinetics shown in FIG. 12A into the tissue volume, RIF concentrations were calculated under the assumption that the amount of daily RIF release from the device into this volume to be treated is equivalent to daily RIF clearance from this volume. For effective treatment of S. aureus biofilms the calculated concentrations must be above the minimal inhibitory concentration (MIC) for planktonic bacteria of ~0.004 mg/L shown in the solid horizontal line.

For prophylactic long-term release the same amount of drug, 18.8 mg rifampicin (20% by weight of rifampicin in 100 µm polymer layer, diameter of frame=25 mm and height=12 mm) with the release kinetics for the prophylactic approach (FIGS. 12A and B) demonstrates that 80% can be released in long-term up to 4 months. Assuming in a worst-case scenario that planktonic bacteria shall be eradicated in an extension of 1 mm in a cylindrical shape around a stent device (e.g., with a diameter of 25 mm) and the antibiotic is present only in this volume (e.g., 1.63 mL) the maximal concentration when released within one day would be 18.8 mg per 1.63 mL, far more than the minimal inhibitory concentration of rifampicin against planktonic S. aureus as demonstrated in FIG. 12B.

Figure 13A:
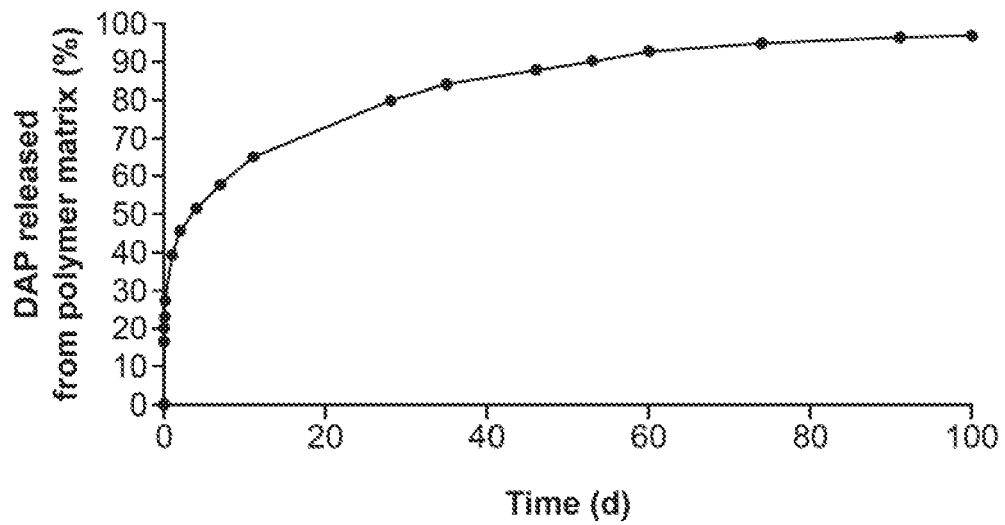
FIG. 13A gives an example of a prophylactic long-term release kinetics of daptomycin embedded in a polydioxanone (X206S) matrix, shown as cumulative daptomycin release over time.

FIG. 13A depicts the curve for prophylactic daptomycin release against S. aureus would be above the MIC level of 0.25 mg/L for about 170 days. Because planktonic Enterococcus faecalis has the same sensitivity against daptomycin as S. aureus (same MIC values of about 0.25 mg/L), the daptomycin response curves against both strains are equal.

A localized therapeutic treatment regimen of the infection allows the exposure of bacterially infected tissue to very high concentrations of an antibiotic, which cannot be obtained by systemic therapy due to toxic side effects. Approximate concentration in tissue with systemic therapy are believed to be as follows: vancomycin 1 mg/L; daptomycin 4 mg/L; rifampicin 1 mg/L.

As used herein, it should be understood that use of the singular throughout this application including the claims includes the plural and vice versa unless expressly stated otherwise. That is, "a" and "the" are to be construed as referring to one or more of whatever the word modifies. Non-limiting example is: "an antibiotic substance" is understood to include one drug or combination of the drug.

As used herein, the preferred targeted bacteria are Staphylococcus aureus, Enterococcus faecalis, and Enterococcus faecium. Other targeted bacteria are, however, also within the scope of the invention, such as streptococci or coagulase-negative staphylococci.

Bacteria, such as those described above, are capable of forming bacterial biofilms. As used herein, bacterial biofilms include bacteria that attach to and grow on surfaces or boundaries (such as liquid gaseous boundary and liquid solid boundary). The surfaces can be biological surfaces or non-biological surface. Biological surfaces include native heart valves or blood vessel or thrombi; and non-biological surfaces include (bio-) prostheses, artificial heart valves, or other implanted materials or devices. The bacteria produce a matrix that can be a composition of various compounds and often includes mucous polysaccharides, proteins, and DNA/RNA. The life form of bacteria in biofilms is substantially different to the very same bacteria that live so-called planktonic, i.e. as single cells or cell agglomerates but not attached to surfaces or boundaries. Compared to planktonic bacteria the bacteria in biofilms have an altered metabolism, which may also be expressed by the release of so called info chemicals (inducer/inhibitor) substances that allow the organisms for example to measure the cell density of the own species) that induce biofilm-formation or expression of certain (secondary) metabolites defense mechanisms.

With respect to the bacteria that cause IE, the formation of biofilms is a severe problem, because the bacteria in biofilms are by orders of magnitude less sensitive to antibiotic substances. This may be due to the mechanical and chemical barrier of the biofilm, which is not easily penetrated by many drugs (antibiotics) so that the concentrations of antibiotic substances in biofilms is reduced. Further, the altered metabolism of bacteria in biofilms may lead to a lower sensitivity of the bacteria to antibiotics. This may in particular be the case when bacterial cells in the biofilm reduce their metabolic rate and enter into a resting state. The mode of action of many antibiotics includes the inhibition of protein turnover, protein synthesis, metabolism, transcription, and formation of cell walls, which means the action of these antibiotics requires an active metabolism, often in particular cell division.

As a consequence, antibiotics are typically much less potent on cells in biofilms (with reduced metabolic rate and protection through the biofilm matrix). In accordance with the embodiments of the present invention, to treat the bacteria in biofilms, higher concentrations of an antibiotic via local delivery is proposed, to penetrate the biofilm matrix and thus reach effective concentrations in the biofilms.

Bacterial biofilms play a central role in IE. *Staphylococcus aureus* and Enterococci species are regularly found in IE biofilms. In addition to the biofilm matrix components that are derived from the bacterial cells, components of the (human) host contribute to the matrix. In addition to non-cellular blood components (proteins, immune globulins, etc.), contributory components include (clotted) erythrocytes and cells of the immune system. This leads to formation of an infective mass, called a "vegetation" or "bacterial vegetation." These vegetations can be located at the site of infection and can regularly increase during disease progression. In some cases, such vegetations can reach a length greater than 20 mm.

A common location of these vegetations is the heart valve leaflets. There, the infective vegetations are in the blood stream and are thus exposed to mechanical stress. As a consequence, parts of the vegetation may break off and infective material is distributed via the blood stream into other organs and tissues where blood vessels may be embolized and further foci of infection are distributed. As a consequence, organ failure e.g. in the kidneys or stroke are common sequelae of IE and often the reason by what the underlying IE is found.

Figure 14:
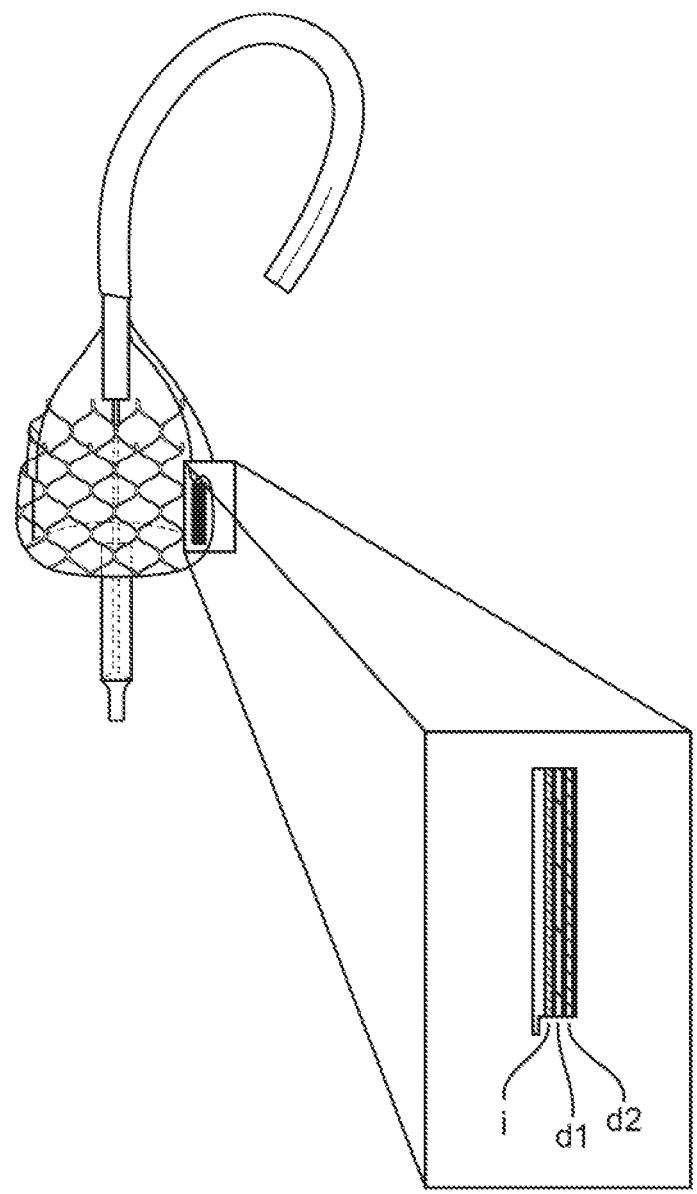
FIG. 14 outlines a heart valve model (drug eluting valve, DEV) with ring-shaped sandwich layers: i=impermeable layer; d1=drug releasing layer with one antibiotic; and d2=drug-releasing layer with a further antibiotic. In a preferred configuration, the layer d1 can be the rapid-releasing layer such as daptomycin-polymer-combination and d2 can be the slower-releasing layer such as rifampicin-polymer-combination.

The foregoing effective antibacterial treatments comprise local delivery of one or more antibiotics to infected issue, the periphery tissue adjacent the infected area, and/or surrounding cardiac tissue. Delivery can be at or adjacent to the mitral valve (bicuspid valve) and the tricuspid valve and the aortic valve. Local delivery can be performed prior to valve replacement procedure—transcatheter aortic valve replacement (TAVR) or transcatheter mitral valve replacement (TMVR), both of which are well known to a person skilled in the art. In another embodiment, local delivery is performed concurrently with the replacement of the valve or with the valve itself, as illustrated by FIG. 14. In another embodiment, local delivery is preformed after the valve replacement procedure. In yet another embodiment, local delivery can encompass any combination of the forgoing timings, e.g., before, during, and/or after the value replacement procedure. In some embodiments, local delivery can be done by a drug delivery catheter, with or without a balloon, with the appropriate expedient or carrier, such as, for example, a solvent, hydrogel, or vascular paving polymer.

In some embodiments, the present invention additionally provides a method to capture and contain the infective vegetations in order to prevent embolization and spread of infective foci, in addition the containment allows to embed the vegetations circumferentially.

Figure 2:
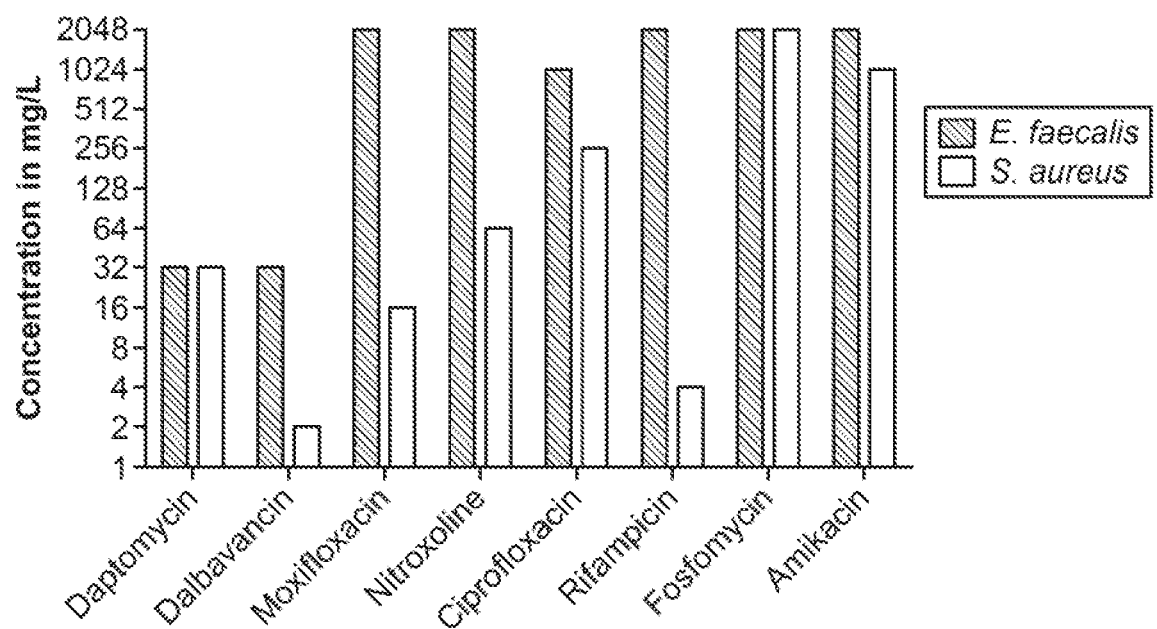
FIG. 2 summarizes biofilm bactericidal concentrations (BBCs) in mg/L of the individually tested antibiotics against *S. aureus* and *E. faecalis* in biofilms. Antibiotics with low BBCs indicate a higher antibacterial potency and are therefore advantageous for local IE treatment. Among the shown antibiotics, the substances daptomycin, rifampicin, and dalbavancin have the highest potency to suppress *S. aureus* and *E. faecalis* in biofilms and are therefore among the preferred antibiotics for local treatment and/or prevention of infective endocarditis.

The antibiotic, in conjunction with all embodiments and teachings of this invention, can be rifampicin, daptomycin, dalbavancin, vancomycin, gentamycin, or any combination of two or more of these agents. For example, the combinations can include including rifampicin and dalbavancin, rifampicin and daptomycin, or rifampicin and vancomycin. As described herein, the present inventors have discovered that the combination of rifampicin, with daptomycin and/or dalbavancin and/or vancomycin is especially effective against bacterial biofilms comprising common bacteria that cause, or are associated with, IE, such as *S. aureus* and/or *E. faecalis* biofilms. In addition, antibiotic drug resistance is reduced by the combination of at least rifampicin plus daptomycin as shown in FIGS. 2 and 3. As also mentioned, the antibiotic, in conjunction with all embodiments and teaching of this invention can be quinolone antibiotics (e.g., fluoroquinolones) and/or penicillinase-resistant beta-lactam antibiotics (e.g., oxacilline), used alone or with any one or combination of rifampicin, daptomycin, dalbavancin, vancomycin, or gentamicin. Any of the aforementioned agents or antibiotics can also include a pharmaceutically acceptable salt or ester thereof. Derivatives or analogs of these antibodies can also be used and falls within the scope of the invention.

Figure 10:
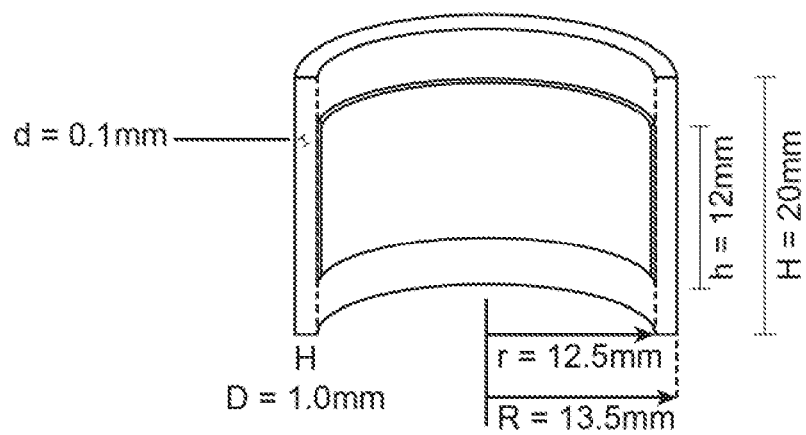
FIG. 10 illustrates a cross section of a theoretical requirements for a prophylactic treatment of IE. The drug-releasing layer, including the impermeable is exemplarily given as d=0.1 mm (e.g., 0.01 mm to 1.0 mm). It is illustrated under the assumption that the volume to be protected from a bacterial infection around a valve or vessel has a cylindrical ring-shaped volume with a radius exceeding 1 mm the radius of the heart valve (h=12.5 mm) and with a height of H=20 mm and that the local therapeutic device has a height h=12 mm, the tissue volume to be prophylactically addressed is 1.63 mL.
Figure 13B:
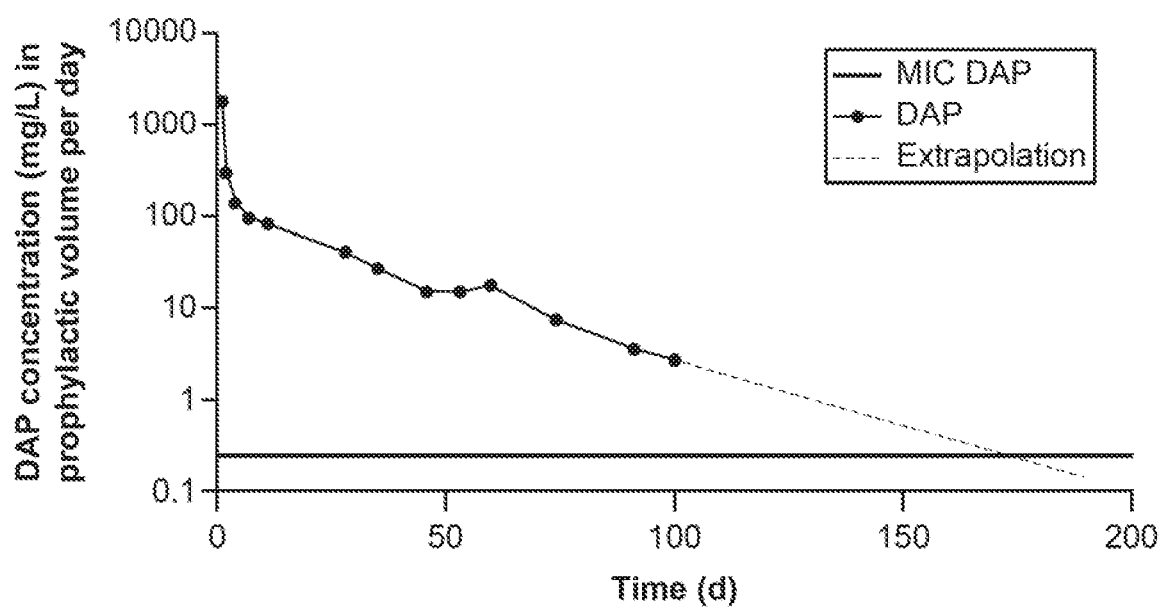
FIG. 13B illustrates a prophylactic long-term concentration profile of daptomycin (DAP) in an assumed cylindrical ring-shaped volume of 1.63 mL (as calculated in FIG. 10) around a vessel or heart valve over time. On the basis of the release kinetics shown in FIG. 13A into the tissue volume, DAP concentrations were calculated under the assumption that the amount of daily DAP release from the device into this volume to be treated is equivalent to daily DAP clearance from this volume. For effective treatment of S. aureus biofilms, the calculated daptomycin concentrations must be above the minimal inhibitory concentration (MIC) for planktonic bacteria of ~0.25 mg/L shown in the solid horizontal line.

For the prevention of IE after replacement of cardiac valves either with open chest surgery or by transcatheter valve, the local drug release can be down regulated because only the attachment of plantonic bacteria in a small value around the implants should be prevented (see, FIG. 10). However, the duration of drug release can be extended to several months until ingrowth of prosthetic material. Therefore, slow-releasing folia may be needed as depicted in FIGS. 12 and 13.

The delivery vehicle of the antibiotic agent can be by a composition comprising a (bio-)polymeric matrix, such as a polylactide, a polylactone, a polyglycolide, a polydioxanone, and combinations, mixtures, derivatives, or copolymers thereof. The matrix can be collagen. The matrix can comprise 50-90%, preferably 70-90%, preferably 70-80% (weight %) of the total weight of the composition and the antibiotic agent or combination of agents can comprise 10-50%, preferably 10-30%, preferably 20-30% (weight %) of the total weight of the composition. Various exemplary release profiles are illustrated in FIG. 7.

The matrix may be in the form of an attachment or coating on a medical device, such as stent-type device, artificial valve, or clips used in valve repair procedures. This is illustrated in FIG. 14. The polymeric matrix can be attached to or coated on a cardiac valve. The cardiac valve can be a prosthetic or homograft cardiac valve, preferably the cardiac valve is a prosthetic cardiac valve. The polymeric matrix can be attached to or coated on a partially opened or closed ring structure. The ring structure is adapted and configured for positioning behind a diseased aortic valve of a patient for local release of the incorporated antibiotic(s), preferably where the patient does not suffer from major aortic valve dysfunction and/or wherein the positioning does not cause major aortic valve dysfunction. The polymeric matrix can be coated on or attached to a transcatheter valve replacement (TVR) system, preferably a transcatheter aortic valve replacement (TAVR) system or a transcatheter mitral valve replacement (TMVR) system.

The polymer may be bioabsorbable, bioresorbable, bioerodable, biodegradable, or biostable. As used herein, the terms "bioabsorbable," "bioresorbable" "bioerodable," and "biodegradable" can be used interchangeably. By "bioabsorbable" or "bioresorbable," it is meant that a polymer, e.g., a polymeric substrate or a polymeric coating can, for example, be absorbed by a subject's body. By "biodegradable," it is meant that a polymer, e.g., a polymeric substrate or a polymeric coating can be disposed of in a subject's body. Biodegradation occurs through hydrolysis, enzymatic reactions, oxidation, and other chemical reactions. Bioabsorption or biodegradation can take place over a relatively short period of time, for example, 1-6 months under physiological conditions. As used herein, a biostable polymer refers to a polymer substrate or coating that is not biodegradable, which is defined above. The term "biostable" is used interchangeably with the term "non-degradable" in the art.

In one preferred embodiment, the matrix polymer (e.g., coating on an implantable medical device) used to locally deliver the antibiotic agent or the combination of the agents include the following:

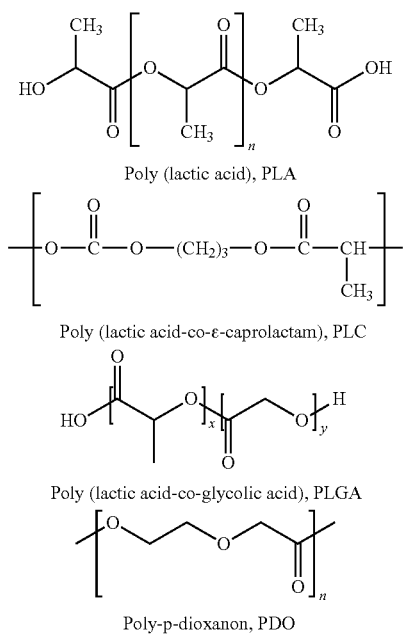

These examples can have the same drug-to-polymer ratios as recited above. It should also be understood the any of the polymers used or discusses herein could be grafted, cross-linked, or provided with modified end groups. A polymeric matrix can also include an electrospun fiber matrix, a melt extrusion fiber matrix, or a melt extrusion fiber matrix disposed onto a biostable polymer (such as polyurethane (PU) or polyethylenterephthalat (PET)) or a metal substrate. Electrospinning can be used to generate biomimetic scaffolds made of synthetic and natural polymers for tissue engineering applications of the present invention for local delivery of an antibiotic agent. In some embodiments, well-known processes including dip-coating or spray coating, with use of appropriate solvents, can also be utilized to coat a device and deliver the agent.

The amount of an agent added to the formulation for making the matrix or the amount of agent that the matrix actually delivers can be, for example, 10-80 milligrams or more narrowly 20-50 milligrams.

The polymeric matrix used as a coating can have more than one layer as illustrated in FIG. 14. In addition to an antibiotic delivery layer, the coating can have a primary layer (for increasing adhesion to a device) and/or a topcoat layer (to reduce the rate of release of the antibiotic). If more than one antibiotic agents is used, both can be incorporated in the same layer or each can be incorporated into a different layer—one positioned on top of the other or part of the device can be coated with one layer having one antibiotic agent and another part of the device can be coated with the same or another layer of a different polymer having another type of antibiotic agent. To obtain unidirectional release of antibiotics and to prevent washout into the bloodstream, an impermeable membrane such as polyurethane, polytetrafluoroethylene or polyethyleneterephthalate can be applied to the implant structure which is then covered with the antibiotic releasing membranes. In FIG. 14, "i" is an impermeable layer, "d1" is a polymer-drug layer with one antibiotic; and "d2" is a polymer-drug layer with a second antibiotic.

EXAMPLES

Example 1

Figure 1B:
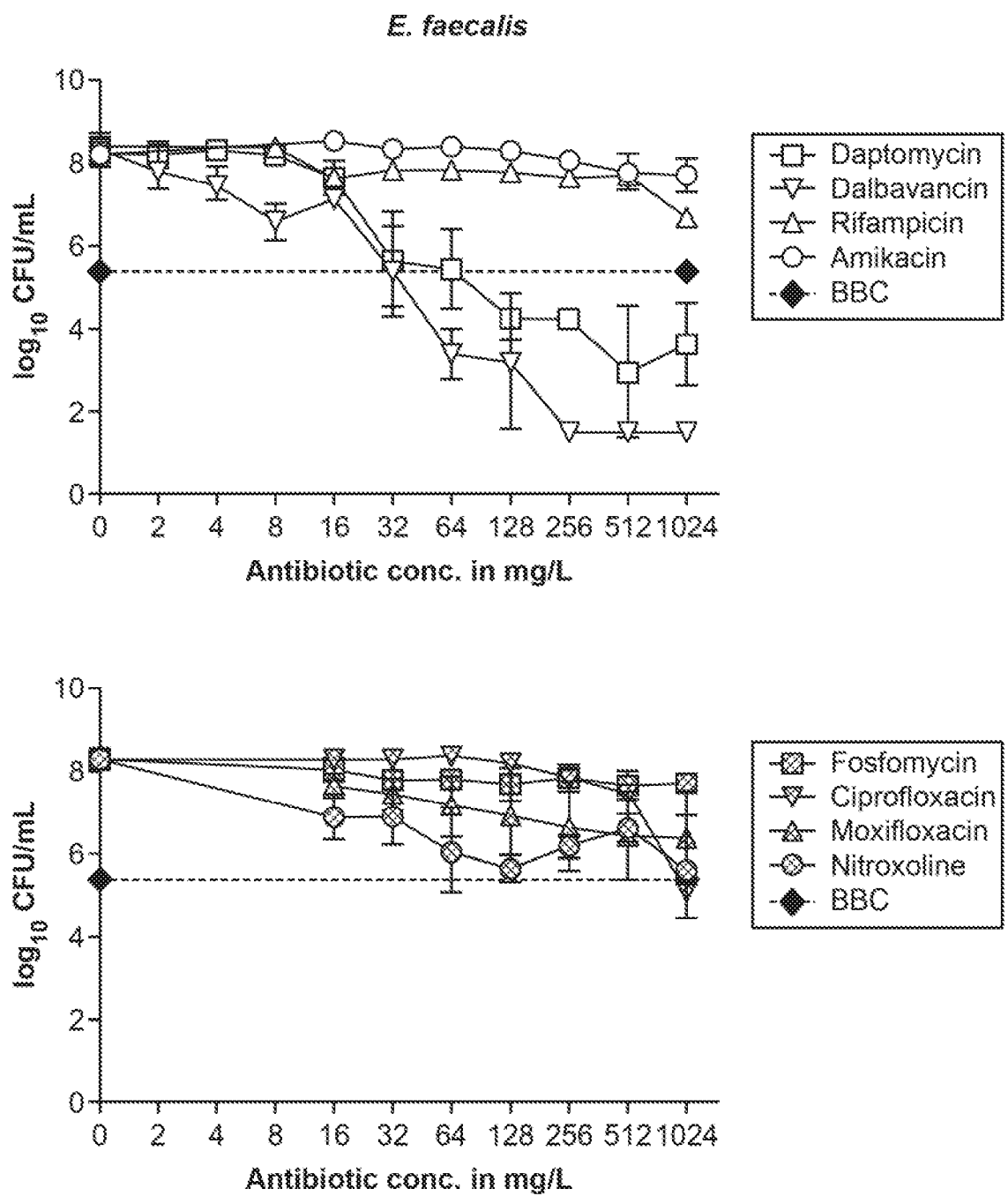

FIGS. 1A and 1B illustrate the effect of different antibiotics tested in a dose-depended manner against bacterial biofilms of different bacterial isolates of *S. aureus* and *E. faecalis* using only one antibiotic per treatment to screen the effect of the single antibiotics against bacterial biofilms. To obtain the results the inventors used four strains of *S. aureus*, i.e. three patient isolates and one reference strain, and three strains of *E. faecalis*, i.e. two isolates from patients as well as one reference strain. In order to test the different antibiotics individually against the bacterial biofilms, the inventors incubated bacterial suspensions of *E. faecalis* and *S. aureus* strains in a 96 well microtiter plate for biofilm formation for 48 hours in a humidified modified atmosphere at 37° C. and 5% $CO_2$ without shaking. For the antibiotic treatment of the biofilms the supernatant of each well was removed and the antibiotic treatment with the individual antibiotics to be tested was added to the biofilms and incubated for 24 hours at the same conditions. The number of bacteria in each well after the 24-hour treatment was determined via so called start-growth-time (SGT) method, where the bacterial regrowth of the dispersed bacteria from the biofilms was measured in an incubation chamber of a plate reader over time. Lower bacteria densities lead to a longer regrowth time to reach a certain threshold compared to controls. Each treatment for each strain was performed in three technical replicates. This procedure was carried out for every strain of *S. aureus* and *E. faecalis* at which the means of the technical replicates are taken together into one line graph and the standard deviation is given as the error bars. Each graph of FIG. 1 reflects the results of multiple experiments. Each line graph illustrates the bacterial count given in the log 10 CFU values per antibiotic concentration in mg/L. The control condition (no antibiotic administration) is given with a value of approximately 8.5 units, shown at an antibiotic concentration of 0 mg/L. The dotted line reflects the so-called biofilm bactericidal concentration (BBC), which means the bacterial cell count of three units of log 10 CFU below the control condition equal to 99.9% reduction of the bacterial cell count, i.e. a value of approximately 5.5 units. When the single graphs cross this BBC line an effective treatment of 99.9% reduction of the bacteria in the biofilms is reached. These experiments show that antibiotic treatment of the bacterial biofilms with only a single antibiotic result in substance specific effects, which are markedly different from tests of the same antibiotics against the same bacteria without biofilms. For example, dalbavancin in FIG. 1 first graph (S. aureus) is very effective with a BBC of about 4 mg/L. In contrast, Amikacin is not effective up to concentrations of 512 mg/L in the same species. Example for E. faecalis: Daptomicin treatment of the biofilms is effective in concentrations of about 32 mg/L similar to dalbavancin, whereas phosphomycin is not effective in the tested concentration range (up to 1024 mg/L). The results obtained from these experiments testing antibiotics bacteria in biofilms strongly differ from those results where antibiotics where tested against planktonic bacteria, which means bacteria are free floating in the medium and not incorporated in a biofilm. Many antibiotics that are active in planktonic bacteria have a strongly reduced or even no potency to eradicate bacteria in biofilms.

Example 2

Figure 3A:
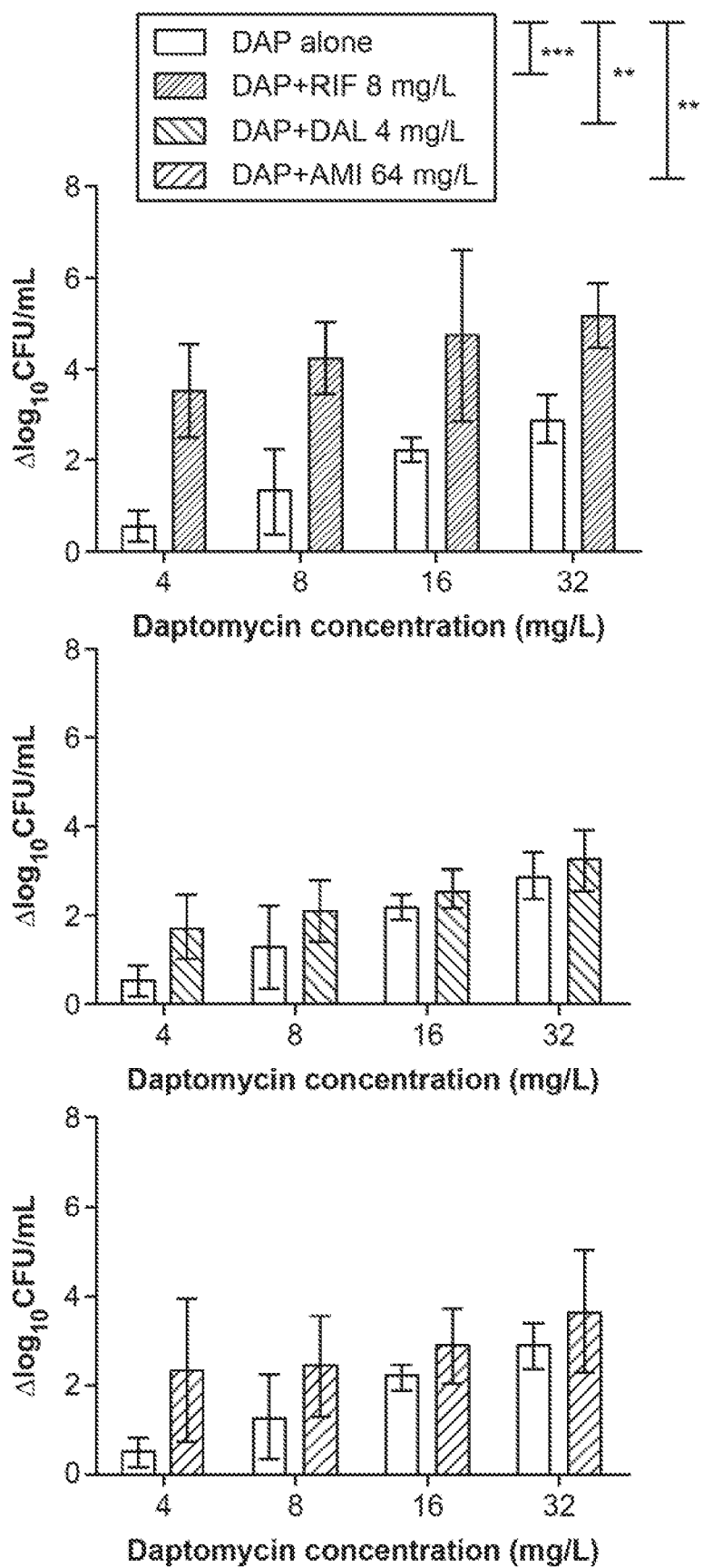
FIGS. 3A-3D illustrate the effects of various combinations of two antibiotics against *S. aureus* in biofilms, where the concentration of one antibiotic is fixed as specified in the legend and the concentration of the other antibiotic is varied according to the values of the abscissa. The ordinate shows the reduction of the colony-forming units in the biofilms given as $\Delta \log_{10}$ CFU, i.e. the difference of the log CFU of the respective antibiotic concentration and the log CFU of the control. Higher valves of $\Delta \log_{10}$ CFU indicate a higher antibiotic potency and are advantageous. (A) daptomycin alone or in combination with rifampicin, dalbavancin, or amikacin. (B) amikacin alone or in combination with daptomycin, dalbavancin, or rifampicin. (C) rifampicin alone or in combination with daptomycin, dalbavancin, or amikacin. (D) dalbavancin alone or in combination with rifampicin, daptomycin or amikacin. Comparison and statistical analysis (two-way-ANOVA) of the efficacy of antibiotic monotherapies and A) daptomycin-, B) amikacin-, C) rifampicin- and D) dalbavancin-combination therapies tested on S. aureus biofilms. Data are shown as mean $\Delta$ log 10 CFU/mL±SD of 4 bacterial strains. * p<0.05,  p<0.01, * p<0.001, ns, non-significant.
Figure 3B:
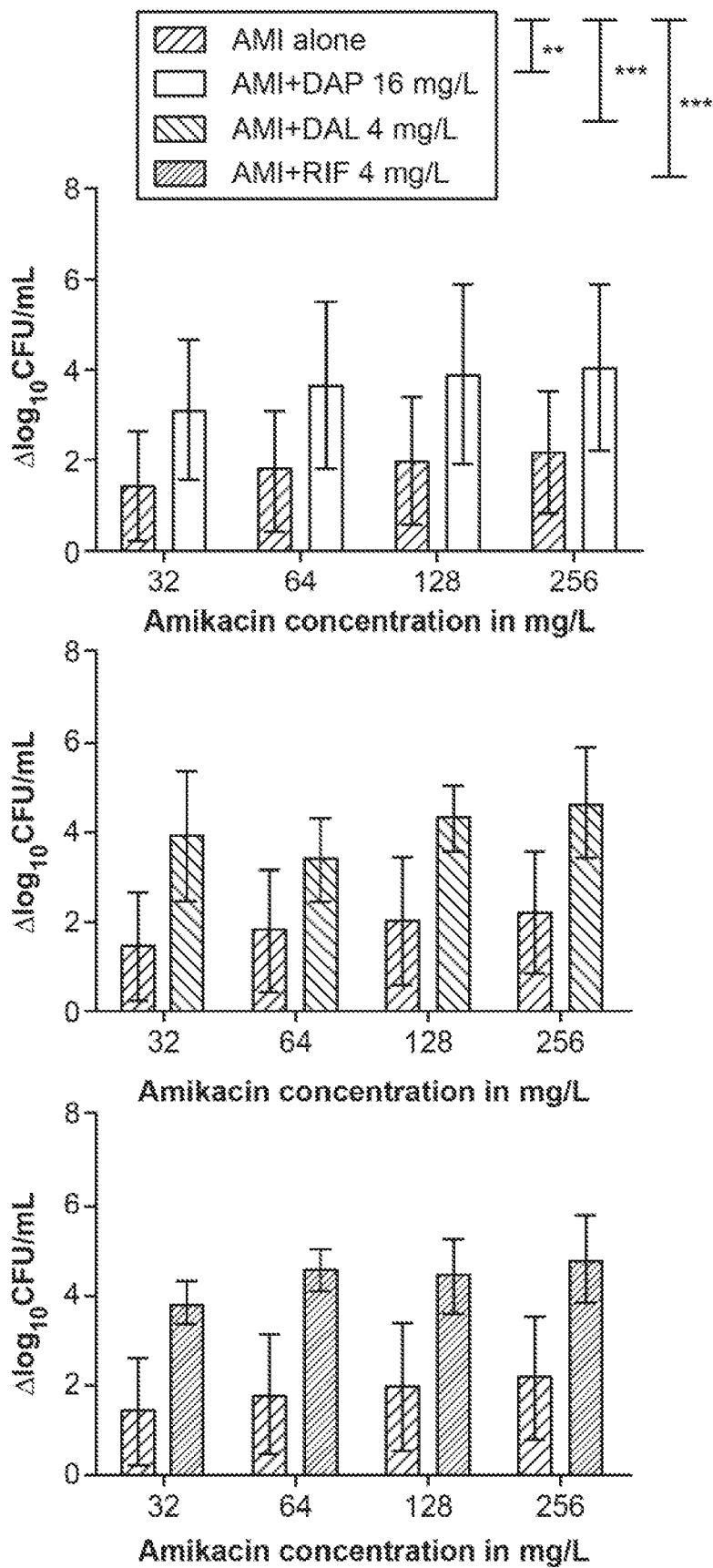
Figure 3C:
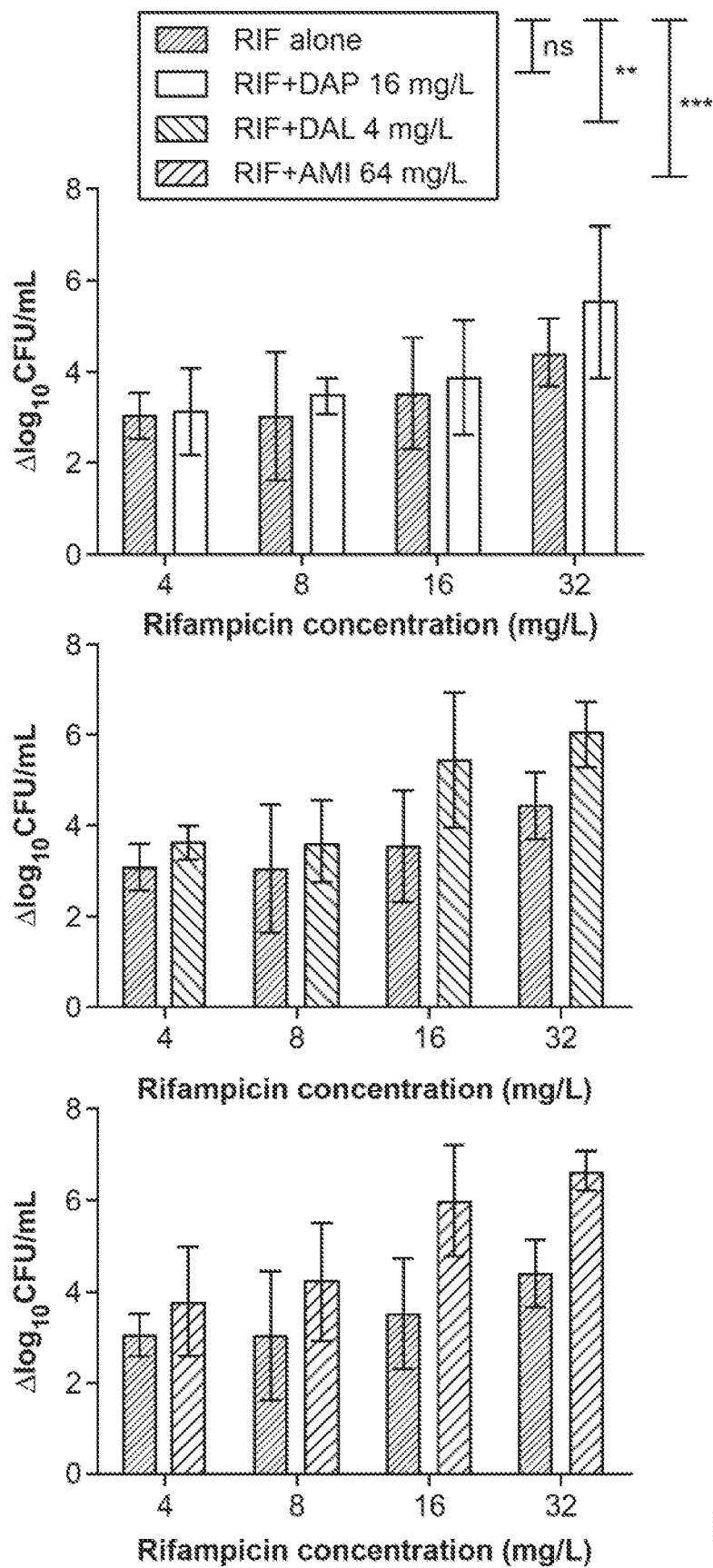
Figure 3D:
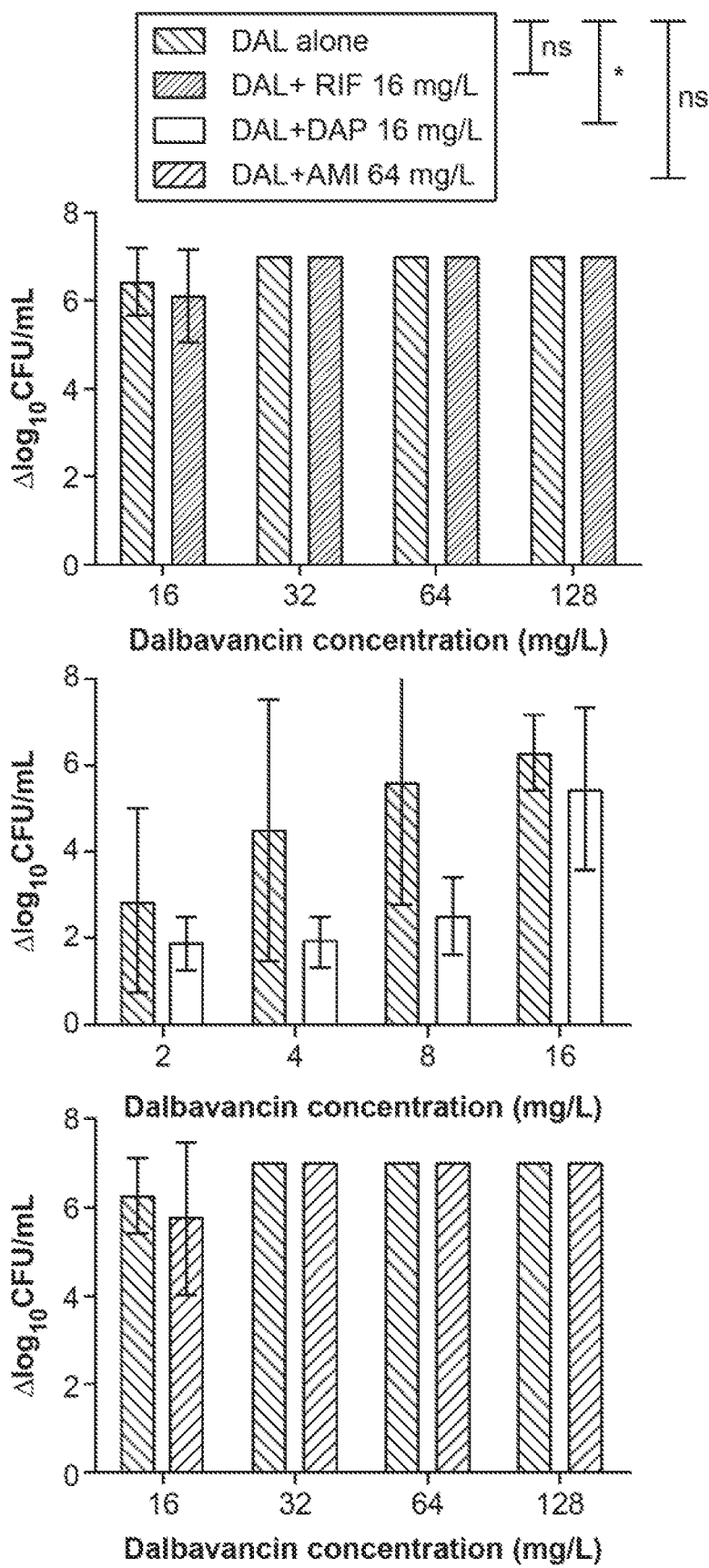
Figure 4A:
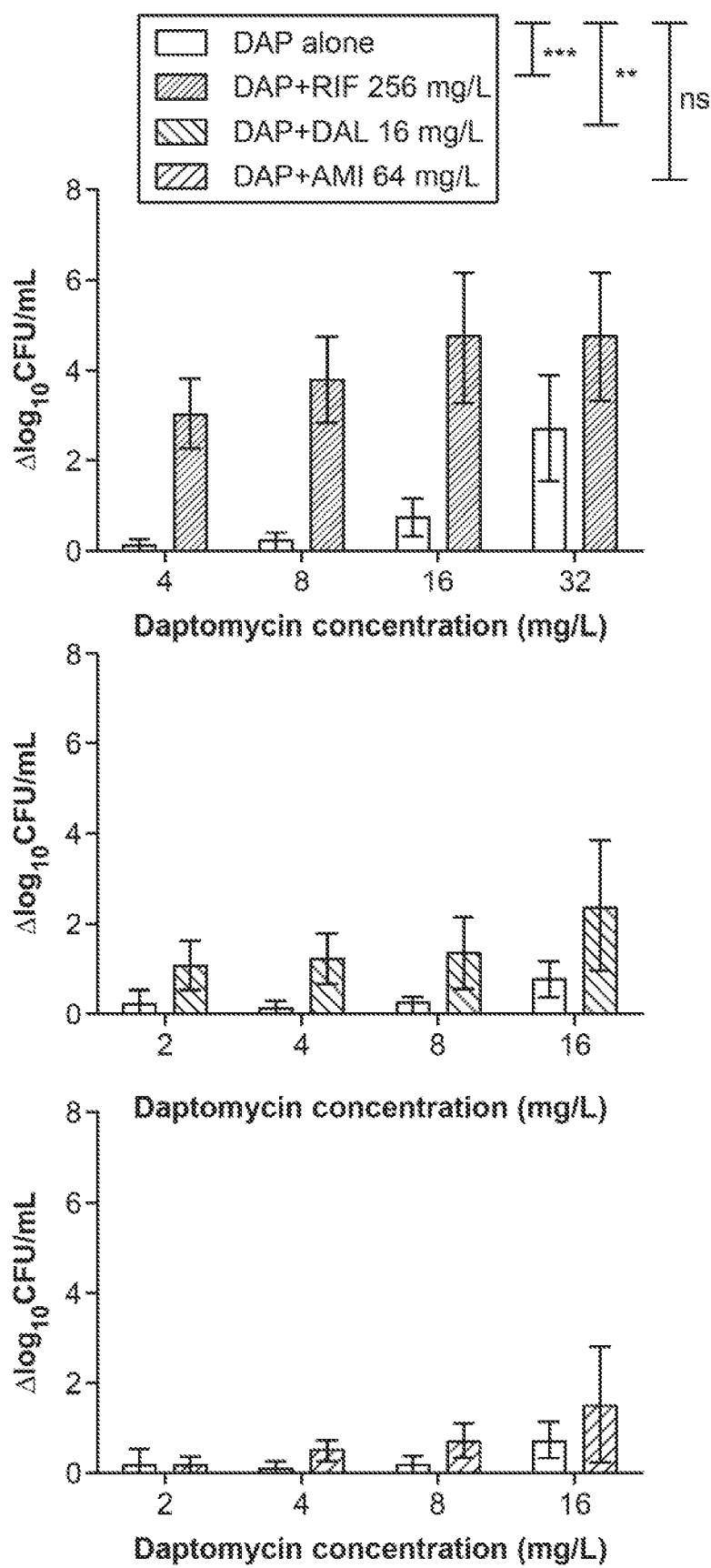
FIGS. 4A-4D illustrate the effects of various combinations of two antibiotics against E. faecalis in biofilms, where the concentration of one antibiotic is fixed as specified in the legend and the concentration of the other antibiotic is varied according to the values of the abscissa. The ordinate shows the reduction of the colony-forming units in the biofilms given as $\Delta \log_{10}$ CFU, i.e. the difference of the log CFU of the respective antibiotic concentration and the log CFU of the control. Higher valves of $\Delta$ log 10 CFU indicate a higher antibiotic potency and are advantageous. (A) daptomycin alone or in combination with rifampicin, dalbavancin, or amikacin. (B) dalbavancin alone or in combination with rifampicin, daptomycin, or amikacin. (C) rifampicin alone or in combination with daptomycin, dalbavancin, or amikacin. (D) amikacin alone or in combination with daptomycin, dalbavancin, or rifampicin. Comparison and statistical analysis (two-way-ANOVA) of the efficacy of antibiotic monotherapies and A) daptomycin-, B) amikacin-, C) rifampicin- and D) dalbavancin-combination therapies tested on E. faecalis biofilms. Data are shown as mean $\Delta$ log 10 CFU/mL±SD of 3 bacterial strains. * p<0.05,  p<0.01, * p<0.001, ns, non-significant.
Figure 4B:
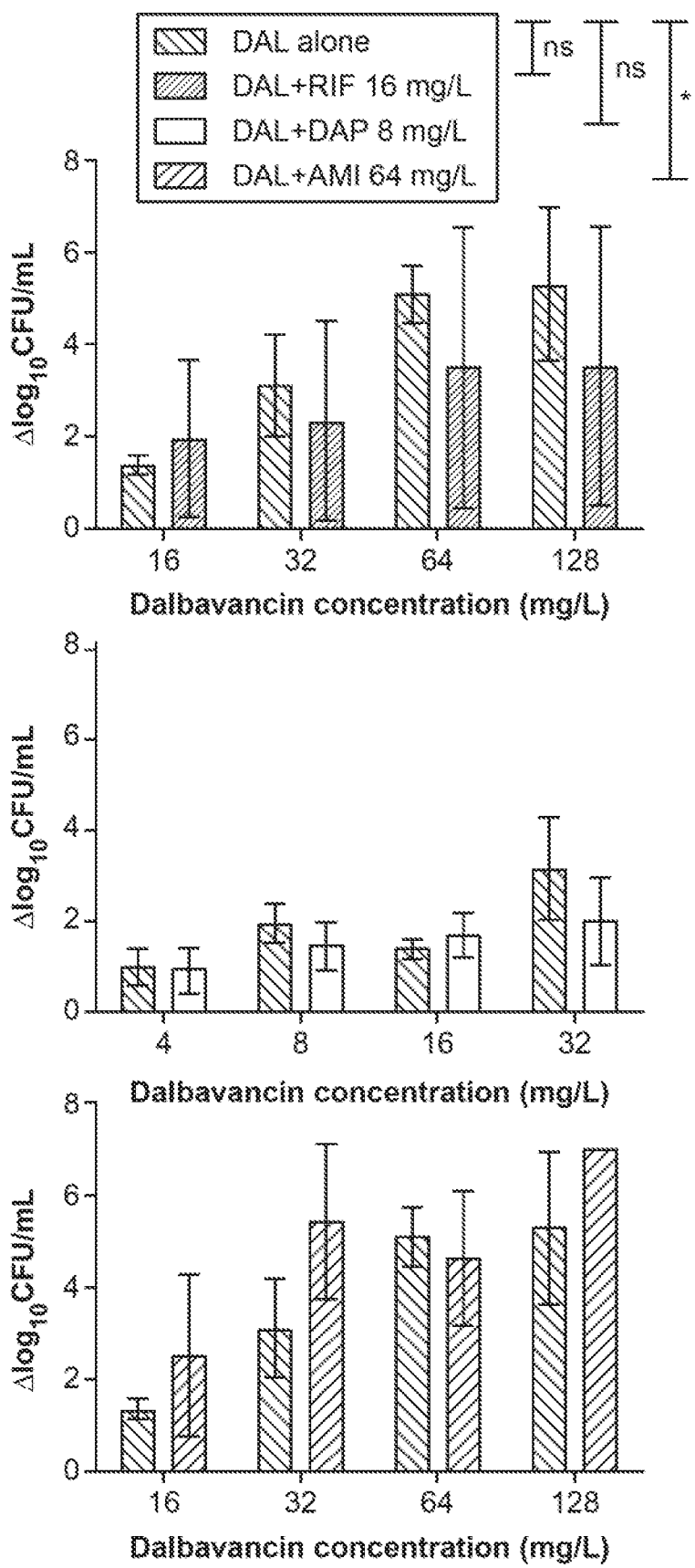
Figure 4C:
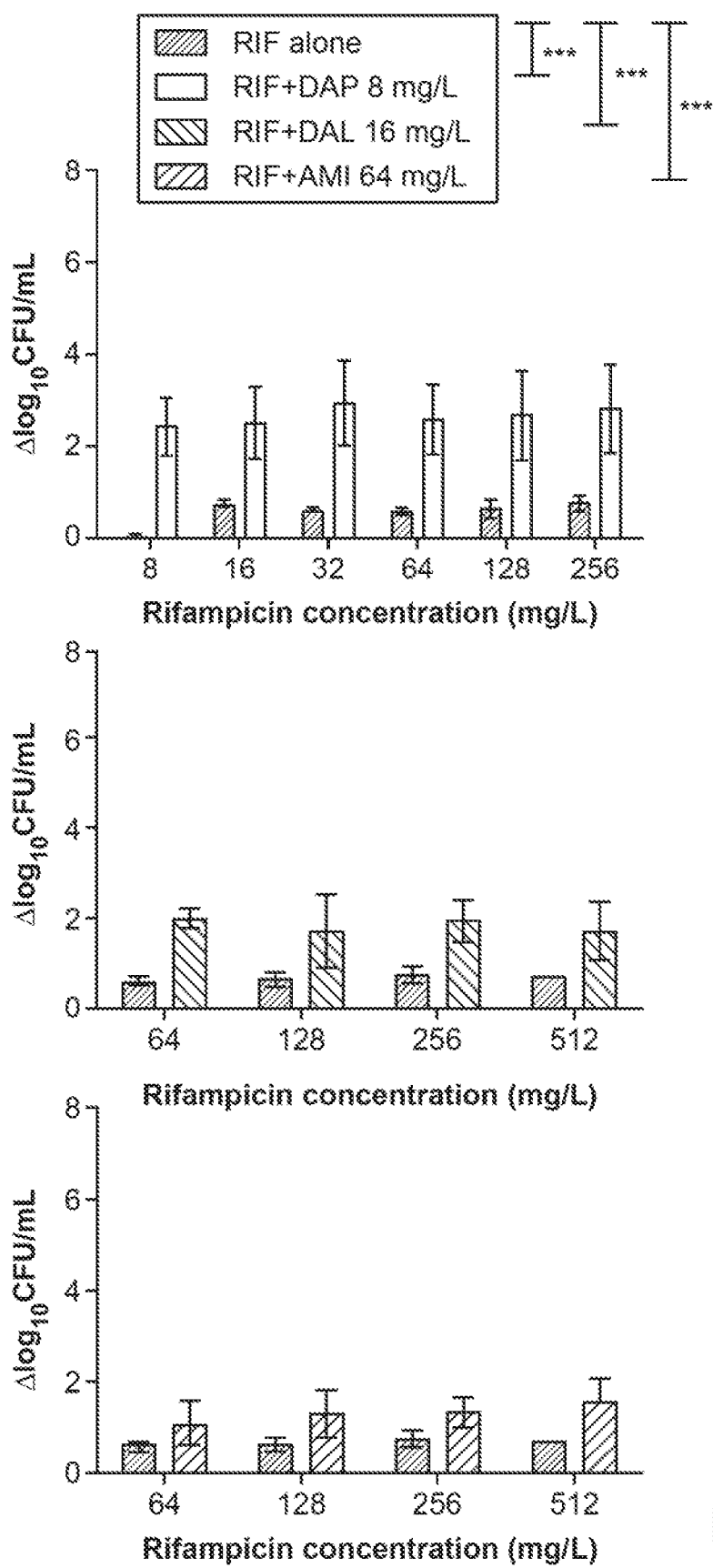
Figure 4D:
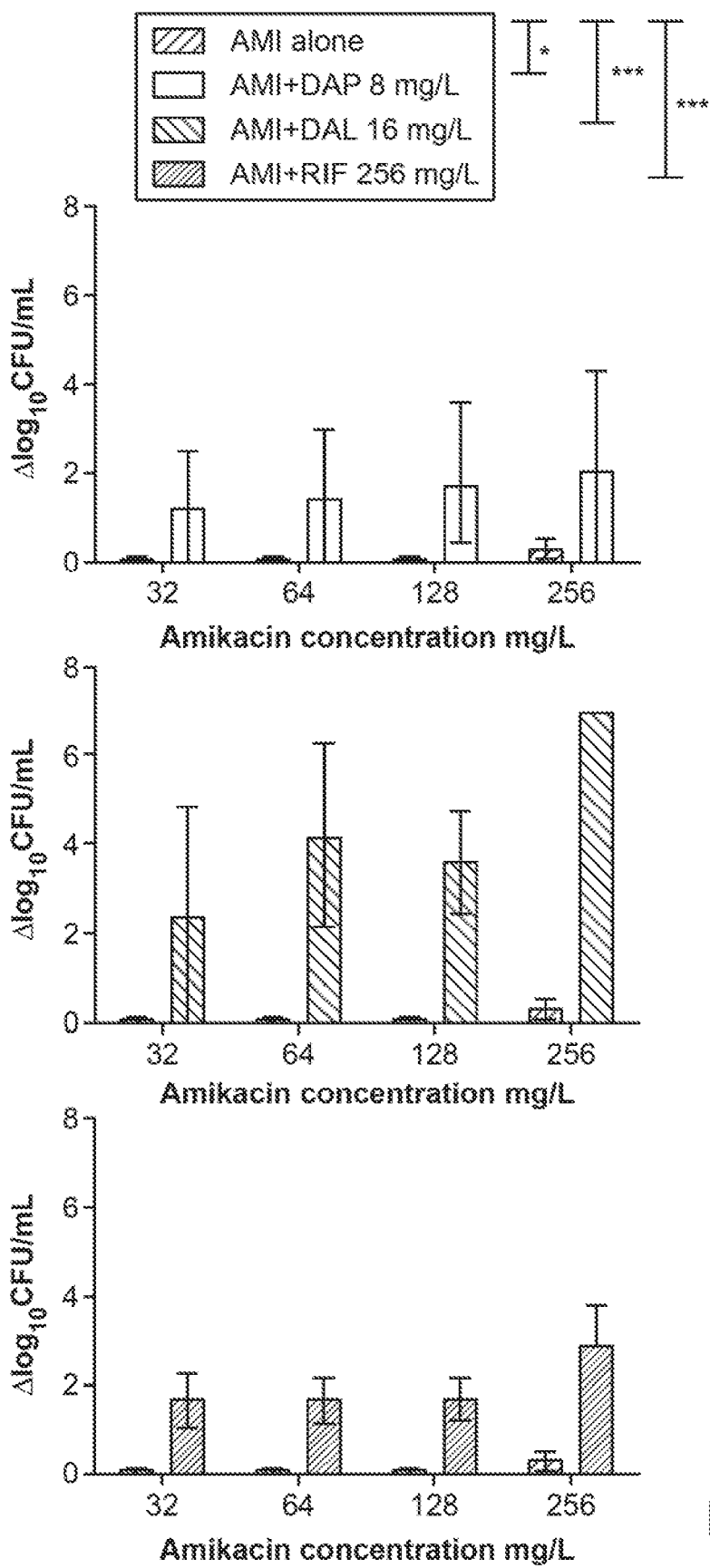

Similar experiments as performed with the single antibiotics shown in FIG. 1 have been carried out for combinations of two antibiotics, which we show in FIGS. 3A-3D and FIGS. 4A-4D to demonstrate possible additive antibiotic effects. In FIGS. 3A-3D the inventors compare the dose-dependent effects of treatments with one antibiotic alone with the addition of a second antibiotic, whose concentration is fixed. The experimental setup was equal to the experiments of FIG. 1. Biofilms were grown for 48 hours before the antibiotic treatment of the biofilm and the supernatant planktonic bacteria were taken away prior to the antibiotic treatment. Again, four different isolates were used for the testing of S. aureus biofilms. In FIG. 3A the combination of DAP with RIF is effective while the combination of DAP and DAL or DAP with AMI has almost no additive effect versus DAP alone. In FIGS. 4A-4D the inventors did the same tests for E. faecalis with two isolates and one reference strain. FIGS. 4A-4D illustrate the effects of various combinations of two antibiotics against E. faecalis in biofilms, where the concentration of one antibiotic is fixed as specified in the legend and the concentration of the other antibiotic is varied according to the values of the abscissa. The ordinate shows the reduction of the colony-forming units in the biofilms given as Δ log 10 CFU. Higher valves of Δ log 10 CFU indicate a higher antibiotic potency. (A) daptomycin alone or in combination with rifampicin, dalbavancin, or amikacin. (B) dalbavancin alone or in combination with rifampicin, daptomycin, or amikacin. (C) rifampicin alone or in combination with daptomycin, dalbavancin, or amikacin. (D) amikacin alone or in combination with daptomycin, dalbavancin, or rifampicin. Again, as in FIG. 3 also in E. faecalis the combination of RIF and DAP show additive effects.

Comparison and statistical analysis (two-way-ANOVA) of the efficacy of antibiotic monotherapies and A) daptomycin-, B) amikacin-, C) rifampicin- and D) dalbavancin-combination therapies tested on E. faecalis biofilms. Data are shown as mean Δ log 10 CFU/mL±SD of 3 isolates. * $p<0.05$,  $p<0.01$, * $p<0.001$, ns, non-significant.

Example 3

In addition to the antibacterial potency of a substance, a major prerequisite for the antibiotic treatment of bacterially infected tissue is that the antiinfective drugs, e.g. antibiotics, released from the implanted device must be able to effectively diffuse into the infected tissue or abscess. Therefore, the inventors studied the diffusion kinetics of various antibiotics in a model of unidirectional diffusion. To mimic the tissue or abscess, the inventors developed a model that consists of a protein gel or alternatively a polysaccharide matrix into which the antibiotics diffuse. A cuvette was filled with this the diffusion matrix and a supernatant layer that contains the antibiotic was added. The diffusion took place horizontally to exclude gravity-driven. The diffusion was measured over a period of 72 hours by UV/VIS absorption at 37° C. at multitudes of 1.4 mm from the starting line. For each antibiotic four independent kinetics were measured. The inventors extracted the data for the distance-depended concentrations of the time-point 24 hours and calculated the mean value for each point with its specific distance to the starting line. The error bars indicate the standard deviation of the independent experiments. FIGS. 6A and 6B illustrate that within 24 hours both antibiotics daptomicin and rifampicin diffuse into the matrix with a distance of 0 mm. The greater of the distance from the starting line the lower are the concentrations of the respective antibiotic. FIGS. 6A and 6B illustrate the mean relative concentrations of the antibiotics daptomicin and rifampicin from these experiments. The starting concentration was set to 100% and the resulting concentrations from the diffusion distances are given relatively to this starting concentration. Rifampicin (FIG. 6B) diffuses slightly faster into the matrix compared to daptomycin (FIG. 6A). This difference may be explained by the strongly differing polarities of the two antibiotic molecules. The polar structure of daptomycin is held back in the polar diffusion matrix, whereas rifampicin is unpolar and may therefore diffuse faster through into matrix. These results are necessary to obtain realistic values of the antibiotic concentrations that are reachable in the infected tissue when released locally from device. Directly at the site of release, which is reflected by the starting line at a distance of 0 mm the highest concentrations can be achieved. In contrast at a distance of 10 mm only about 20% to 30% of the antibiotic concentrations can be achieved within one day and under the assumption that not even transient accumulation occurs. The results from these experiments where used to calculate the minimal and maximal achievable concentrations within a given tissue cylinder to be treated with our local therapy, where the calculated maxima reflect the antibiotics' concentrations in a diffusion distance range of 0-1.4 mm and the calculated minima reflect the antibiotics' concentrations in a diffusion distance of 8.4 to 9.8 mm.

Example 4

Figure 5:
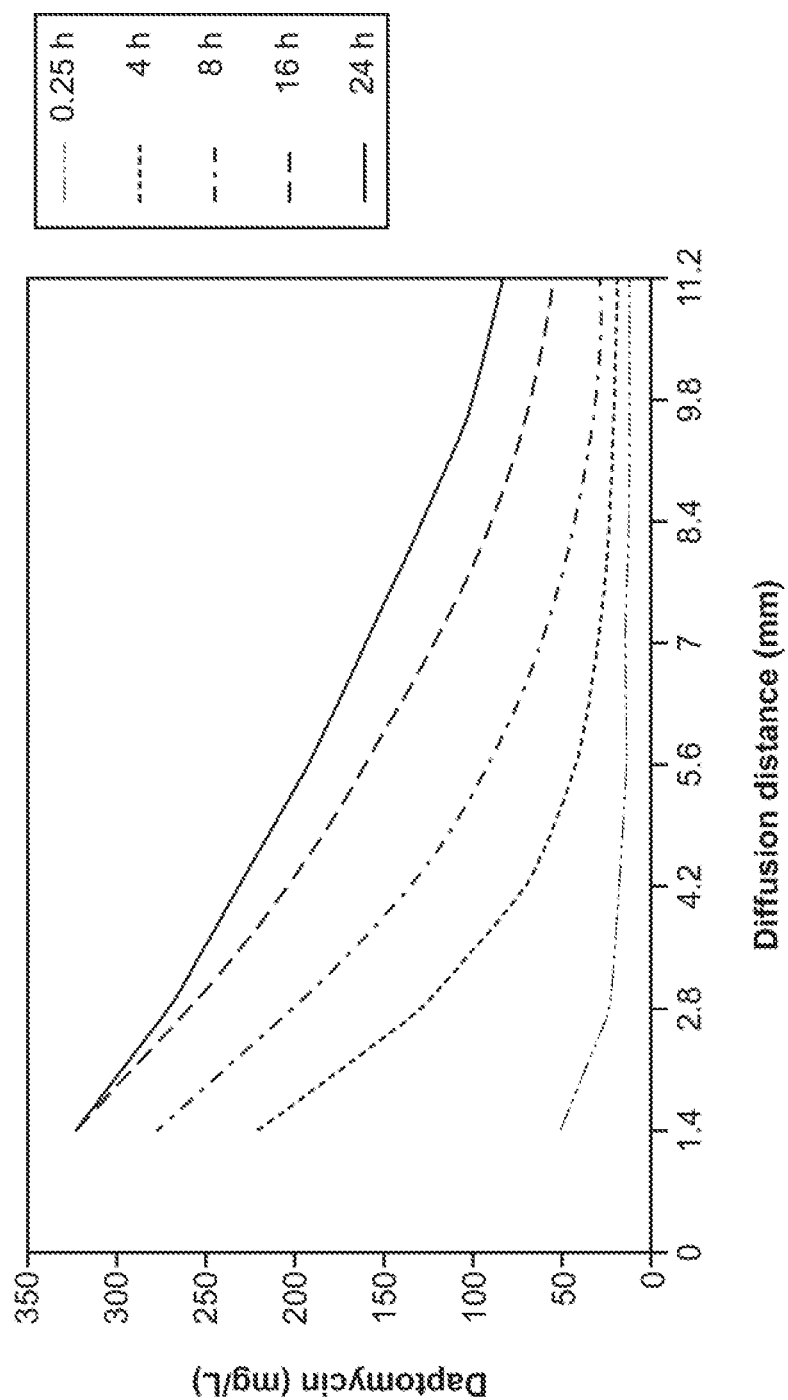
FIG. 5 illustrates the daptomycin concentrations in dependence of the diffusion distance in a collagen matrix at physiological pH from the starting line (0 mm) at various timepoints (time range shown from 0.25 h to 24 h) from a single diffusion experiment. The daptomycin concentrations decrease with increasing distance but reach about 25% of the concentration at 10 mm distance as compared to the distance close to the starting line after a diffusion time of 24 h.

FIG. 5 illustrates the daptomycin concentrations in dependence of the diffusion distance in collagen from the starting line (0 mm) at various time-points (time range shown from 0.25 h to 24 h) from a single diffusion experiment. The daptomycin concentrations decrease with increasing distance but reach about 25% of the concentration at 10 mm distance as compared to the distance close to the starting line after 24 h.

Example 5

FIG. 11 represents a concentration profile of rifampicin (RIF) for therapeutic short-term release in an assumed cylindrical ring-shaped volume (abscess) of 22 mL around a vessel or heart valve over time. On the basis of the release kinetics shown in FIG. 8 into the tissue volume, RIF concentrations were calculated under the assumption that the amount of daily RIF release from the device into this volume to be treated is equivalent to daily RIF clearance from this volume. For effective treatment of *S. aureus* biofilms the calculated concentrations must be above the biofilm bactericidal concentration (BBC) of ~4 mg/L shown in the solid horizontal line. The calculation shows that the rifampicin concentration generated from the local release into this volume is above the BBC for more than 20 days. If in contrast to a homogeneous distribution of the antibiotics the diffusion from the antibiotic-releasing matrix into the cylindrical volume is taken into account, there will be a concentration gradient from the inner (central) to the outer (peripheral) layers of the cylinder. The max and min concentrations are calculated according to the daily diffusion distance of rifampicin in a phosphate-buffered collagen matrix according to FIG. 6 B and reflect the concentric spatial distribution of the antibiotics concentrations within the defined cylindrical volume. The BBC line reflects the biofilm bactericidal concentration of rifampicin from FIGS. 1 and 2.

One having ordinary skill in the art will readily understand that the invention as discussed above may be practiced with steps in a different order, and/or with elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention.

We claim:

1. A method of treating or preventing endocarditis in a human patient in need of therapy, comprising:
    identifying a patient inflicted with or being at risk of contracting *Staphylococcus aureus, Enterococcus faecalis*, or *Enterococcus faecium* at or about a heart valve; and
    locally applying to or in the vicinity of the heart valve a therapeutically or prophylactically effective amount of an agent consisting of rifampicin, daptomycin, dalbavancin, vancomycin, or gentamycin, or any combination of 2 or more of rifampicin, daptomycin, dalbavancin, vancomycin, and gentamycin, wherein the local application of the agent is by an implantable medical device having a coating including an impermeable polymeric inner layer over which an outer layer of the agent is disposed such that impermeable layer is configured to prevent washout of the agent into the blood stream for direct local application of the agent at or about the heart valve.

2. The method of claim 1, wherein the method comprises treatment or prevention of a bacterial biofilm on the endocardium caused by *Staphylococcus aureus, Enterococcus faecalis*, or *Enterococcus faecium*.

3. The method of claim 1, wherein the layer of the agent for local application is a composition comprising a polymer matrix such that the polymer matrix comprises 70-90 weight % of the total weight of the composition and the rifampicin, daptomycin, dalbavancin, vancomycin, gentamycin, or a combination thereof comprises 10-30 weight % of the total weight of the composition.

4. The method of claim 1, wherein the layer of the agent for local application is a composition comprising a polymer matrix such that the polymer matrix comprises 50-90 weight % of the total weight of the composition and the rifampicin, daptomycin, dalbavancin, vancomycin, gentamycin, or a combination thereof comprises 10-50 weight % of the total weight of the composition.

5. The method of claim 1, wherein rifampicin is applied in combination with dalbavancin.

6. The method of claim 1, wherein rifampicin is applied in combination with daptomycin.

7. The method of claim 1, wherein a total amount of rifampicin, daptomycin, dalbavancin, vancomycin, gentamycin, or a combination thereof is locally applied for a course of up to 14 days or 21 days.

8. The method of claim 1, wherein rifampicin, daptomycin, dalbavancin, vancomycin, gentamycin, or a combination thereof is locally applied for a course of 14 or 21 days to 4 months.

9. The method of claim 1, wherein the device is a replacement heart valve for the aortic valve.

10. The method of claim 1, wherein the layer of the agent for the local application is a polymer matrix selected from a group consisting of an electrospun fiber matrix, a melt extrusion fiber matrix, and a melt extrusion fiber matrix disposed onto a biostable polymer or metal substrate.

11. The method of claim 1, wherein the valve is a bicuspid valve.

12. The method of claim 1, wherein at least 80% of the amount of rifampicin, daptomycin, dalbavancin, vancomycin, gentamycin, or a combination thereof is locally applied for a course of up to 14 days or 21 days.

13. The method of claim 1, wherein the agent consists of daptomycin.

14. The method of claim 1, wherein the agent consists of rifampicin.

\* \* \* \* \*